US008828667B2

(12) United States Patent
Siegel et al.

(10) Patent No.: US 8,828,667 B2
(45) Date of Patent: Sep. 9, 2014

(54) METHODS AND COMPOSITIONS RELATING TO ISOCYANATE CONJUGATES

(75) Inventors: Paul D. Siegel, Morgantown, WV (US); Tinashe Blessing Ruwona, Fairmont, WV (US); Donald H. Beezhold, Morgantown, WV (US); Victor Johnson, Morgantown, WV (US); Detlef Schmechel, Laage Ot Kronskamp (DE)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 666 days.

(21) Appl. No.: 12/577,241

(22) Filed: Oct. 12, 2009

(65) Prior Publication Data

US 2010/0099201 A1    Apr. 22, 2010

Related U.S. Application Data

(60) Provisional application No. 61/104,429, filed on Oct. 10, 2008.

(51) Int. Cl.
*G01N 33/53* (2006.01)
*C07K 16/44* (2006.01)

(52) U.S. Cl.
USPC .......... 435/7.1; 435/7.92; 435/7.94; 436/506; 530/388.1; 530/388.9

(58) Field of Classification Search
None
See application file for complete search history.

(56) References Cited

U.S. PATENT DOCUMENTS 4,383,984 A * 5/1983 Karol et al. .................... 436/545

OTHER PUBLICATIONS

Harlow et al, in Antibodies a Laboratory Manual, 1988, Cold Spring harbor laboratory publication, Cold Spring Harbor, NY, p. 91-94 and 141-153.*
Wisnewski, A. et al., Identification of Human Lung and Skin Proteins Conjugated with Hexamethylene Diisocyanate in Vitro and in Vivo, *American Journal of Respiratory and Critical Care Medicine*, 162: 2330-36, 2000.
Johnson, V. et al., Inhalation of Toluene Diisocyanate Vapor Induces Allergic Rhinitis in Mice, *The Journal of Immunology*, 179: 1864-71, 2007.
Karol, M., Respiratory Effects of Inhaled Isocyanates, *CRC Critical Reviews in Toxicology*, 16(4): 349-379, 1986.
Johannesson, G. et al., Identification and characterisation of adducts between serum albumin and 4,4'-methylenediphenyl diisocyanate (MDI) in human plasma, *Archives of Toxicology*, 78: 378-83, 2004.
Kristiansson, M. et al., Determination of hexahydrophthalic anhydride adducts to human serum albumin, *Biomarkers*, 8(5): 343-59, Sep.-Oct. 2003.
Mraz, J. et al., 2,4-Toluenediisocyanate and hexamethylenediisocyanate adducts with blood proteins: assessment of reactivity of amino acid residues in vitro, *Chemico-Biological Interactions*, 117: 173-86, 1999.
Redlich, C. et al., Airway isocyanate-adducts in asthma induced by exposure to hexamethylene diisocyanate, *Scandinavian Journal of Work, Environment and Health*, 23: 227-31, 1997.
Wisnewski, A. et al., Human innate immune responses to hexamethylene diisocyanate (HDI) and HDI-albumin conjugates, *Clinical and Experimental Allergy*, 38: 957-67, 2008.
Wisnewski, A. et al., Isocyanate vapor-induced antigenicity of human albumin, *The Journal of Allergy and Clinical Immunology*, 113(6): 1178-84, Jun. 2004.
Wisnewski, A. et al., Isocyanate-conjugated human lung epithelial cell proteins: A link between exposure and asthma?, *Journal of Allergy and Clinical Immunology*, 104(2): 341-47, 1999.
Wisnewski, A. et al., Glutathione protects human airway proteins and epithelial cells from isocyanates, *Clinical and Experimental Allergy : Journal of the British Society for Allergy and Clinical Immunology*, 35: 352-57, 2005.
[Author unknown], Guide for the Care and Use of Laboratory Animals, *Institute of Laboratory Animal Resources*, 1996, pp. 1-128.
Ye, Y. et al., Cytokeratin Autoantibodies: Useful Serologic Markers for Toluene Diisocyanate-Induced Asthma, *Yonsei Medical Journal*, 47(6): 773-81, 2006.
Lange, R. et al., Toluene Diisocyanate Colocalizes with Tubulin on Cilia of Differentiated Human Airway Epithelial Cells, *Toxicological Sciences*, 50: 64-71, 1999.
Hettick, J. et al., Structural Elucidation of Isocyanate-Peptide Adducts Using Tandem Mass Spectrometry, *Journal of the American Society for Mass Spectrometry*, 20: 1567-75, 2009.
Jin, R. et al., Toluene Diisocyanate Protein Adducts in the Bronchoalveolar Lavage of Guinea Pigs Exposed to Vapors of the Chemical, *Chemical Research in Toxicology*, 6: 906-12, 1993.
Lemus, R. et al., Development of Immunoassays for Biomonitoring of Hexamethylene Diisocyanate Exposure, *Environmental Health Perspectives*, 109(11): 1103-08, Nov. 2001.
Ulrich, H., 2.1.5 Applications of Aliphatic Diisocyanates, *Chemistry and Technology of Isocyanates*, pp. 356-447, 1996.
Kirk-Othmer, et al., Isocyanates, Organic, *Encyclopedia of Chemical Technology*, 5th Ed., pp. 1-28, J. Wiley & Sons, New Jersey, 2004.
Brown, W. et al., Biochemistry of Protein-isocyanate Interactions: A Comparison of the Effects of Aryl vs. Alkyl Isocyanates, *Environmental Health Perspectives*, 72: 5-11, 1987.
Allport, D. et al., Chapter 3: Health in MDI and TDI:Safety, Health and the Environment: A Source Book and Practical Guide; Wiley: 2003.

(Continued)

*Primary Examiner* — Phuong Huynh
(74) *Attorney, Agent, or Firm* — Gifford, Krass, Sprinkle, Anderson & Citkowski, P.C.

(57) ABSTRACT

Compositions are provided according to embodiments of the present invention which include an isolated antibody or antigen binding antibody fragment characterized by binding specificity for a conjugate which is a reaction product of a protein moiety and an isocyanate moiety. Methods of detecting diisocyanate-protein conjugates in a sample are provided according to embodiments of the present invention which include contacting a sample with one or more isolated antibodies or antigen binding antibody fragments characterized by binding specificity for corresponding diisocyanate-protein conjugate antigens.

5 Claims, 9 Drawing Sheets

(56) References Cited

OTHER PUBLICATIONS

Holgate, S. T., Pathogenesis of Asthma. *Clin. Exp. Allergy*, 8: 872-897, 2008.

Lemanske, R. et al., 6. Asthma, *J. Allergy Clin. Immunol.* 111: S502-S519, 2003.

Ott, M. et al., Issues in Diisocyanate Antibody Testing, *Critical Reviews in Toxicology*, 37: 567-585, 2007.

Wisnewski, A. et al., Recent Developments in Diisocyanate Asthma. *Curr. Opin. Allergy Clin. Immunol.*, 1: 169-175, 2001.

Herrick, C. et al., A novel mouse model of diisocyanate-induced asthma showing allergic-type inflammation in the lung after inhaled antigen challenge, *J. Allergy Clin. Immunol.*, 109: 873-878, 2002.

Chipinda, I. et al., Kinetics and Mechanistic Studies of the Hydrolysis of Diisocyanate-Derived Bis-thiocarbamates of Cysteine Methyl Ester, *Chemical Research in Toxicology*, 19: 341-350, 2006.

Park, H. et al., Specific immunoglobulin E and immunoglobulin G antibodies to toluene diisocyanate-human serum albumin conjugate: useful markers for predicting long-term prognosis in toluene diisocyanate-induced asthma, *Clin. Exp. Allergy*, 32: 551-555, 2002.

Karol, M. et al., Tollyl-specific IgE antibodies in workers with hypersensitivity to toluene diisocyanate, *Am. Ind. Hyg. Assoc. J.*, 39: 454-458, 1978.

Cartier, A. et al., Specific serum antibodies against isocyanates: association with occupational asthma, *J. Allergy Clin. Immunol.*, 84: 507-514, 1998.

Campo, P. et al., Diisocyanate conjugate and immunoassay characteristics influence detection of specific antibodies in HDI-exposed workers, *Clin. Exp. Allergy*, 37: 1095-1102, 2007.

Son, M. et al., Heterogeneity of igE Response to TDI-HSA Conjugates by ELISA in Toluene Diisocyanate (TDI)-induced Occupational Asthma (OA) Patients, *J. Korean Med. Sci.*, 13, 147-152, 1998.

Tee, R. et al., Specific IgE to isocyanates: A useful diagnostic role in occupational asthma, *J. Allergy Clin. Immunol.*, 101: 709-715, 1998.

Welinder, H. et al., IgG antibodies against polyisocyanates in car painters, *Clin. Allergy*, 18: 85-93, 1998.

Jones, M. et al., Is occupational asthma to diisocyanates a non-IgE-mediated disease?, *J. Allergy Clin. Immunol.*, 117: 663-669, 2006.

Park, H. et al., Specific IgG, but not specific IgE, antibodies to toluene diisocyanate-human serum albumin conjugate are associated with toluene diisocyanate bronchoprovocation test results, *J. Allergy Clin. Immunol.*, 104: 847-851, 1999.

Bernstein, D. et al., Evaluation of antibody binding to diisocyanate protein conjugates in a general population, *Ann. Allergy Asthma Immunol.*, 97: 357-364, 2006.

Pauluhn, J. et al., Analysis of biomarkers in rats and dogs exposed to polymeric methylenediphenyl diisocyanate (pMDI) and its glutathione adduct, *Toxicology*, 222: 202-212, 2006.

Brown, W. et al., Biomarkers of Toluene Diisocyanate Exposure, *Appl. Occup. Environ. Hyg.*, 17: 840-845, 2002.

Wisnewski, A., Developments in laboratory diagnostics for isocyanate asthma, *Curr. Opin. Allergy Clin. Immunol.*, 7: 138-145, 2007.

Nethercott J., Practical Problems in the Use of Patch Testing in Evaluation of Patients with Contact Dermatitis, *Current Problems in Dermatology II*, 97-123, 1990.

Wigger-Alberti, W. et al., Contact Dermatitis Due to Irritation, p. 1-9, in Adams, R., *Occupational Skin Diseases*, Saunders, 3rd edition, 1999.

Fischer, T. et al., Diagnostic Patch-Testing, p. 221-235, in *Occupational Skin Diseases*, Saunders, 3rd edition, 1999.

Chappelle, A. et al., Some Limitations in the Use of Urine Biomonitering for Measuring TDI Exposure, Isocyanates: Sampling, Analysis and Health Effects, 64-74, 2008.

Sennbro, C. et al., Biological monitoring of exposure to toluene diisocyanate, *Scand. J. Work Environ. Health*, 30: 371-378, 2004.

Tinnerberg, H. et al., Air and Biological Monitoring of Toluene Diisocyanate in a Flexible Foam Plant, *Am. Ind. Hyg. Assoc. J.*, 58: 229-235, 1997.

Dalene, M. et al., Biological monitoring of hexamethylene diisocyanate by determination of 1,6-hexamethylene diamine as the trifluoroethyl chloroformate derivative using capillary gas chromatography with thermoionic and selective-ion monitoring, *J. Chromatogr. B Biomed. Appl.*, 656: 319-328, 1994.

Sabbioni, G. et al., Haemoglobin adducts of aromatic amines: diamines and polyaromatic amines, *Journal of Chromatography B-Analytical Technologies in the Biomedical and Life Sciences*, 744: 377-387, 2000.

Tinnerberg, H. et al., Usage of Air Monitoring and Biomarkers of Isocyanate Exposure to Assess the Effect of a Control Intervention. *Ann. Occup. Hyg.*, 52: 187-194, 2008.

Sabbioni, G. et al., Isocyanate-Specific Hemoglobin Adduct in Rats Exposed to 4,4'-Methylenediphenyl Diisocyanate, *Chemical Research in Toxicology*, 13: 82-89, 2000.

Habeeb, A. et al., Molecular structural effects produced in proteins by reaction with succinic anhydride, *Biochim. Biophys. Acta*, 29: 587-593, 1958.

Stoscheck, C., Quantitation of protein. *Methods Enzymol.*, 182: 50-68, 1990.

Zor, T. et al., Linearization of the Bradford Protein Assay Increases its Sensitivity: Theoretical and Experimental Studies, *Anal. Biochem.*, 236: 302-308, 1996.

Sashidhar, R. et al., Quantitation of Epsilon-Amino Group Using Amino-Acids As Reference-Standards by Trinitrobenzene Sulfonic-Acid—A Simple Spectrophotometric Method for the Estimation of Hapten to Carrier Protein Ratio, *Journal of Immunological Methods*, 167: 121-127, 1994.

Bernstein, D. et al., Guidelines for Preparation and Characterization of Chemical-Protein Conjugate Antigens. Report of the Subcommittee on Preparation and Characterization of Low Molecular Weight Antigens, *J. Allergy Clin. Immunol.*, 84: 820-822, 1989.

Snyder, S. et al., An Improved 2,4,6-Trinitrobenzenesulphonic acid Method for the Determination of Amines, *Analytical Biochemistry*, 64(1): 284-288, 1975.

Lateef, S. et al., An Improved Protocol for Coupling Synthetic Peptides to Carrier Proteins for Antibody Production Using DMF to Solubilize Peptides. *J. Biomol. Tech.*, 18: 173-176, 2007.

Takahashi, S. et al., Regeneration of Amino-Compounds from the 2,4,6-Trinitrophenyl Derivatives by Treatment with Hydrazine, Chemistry Letters, 127-130, 1984.

Schmechel, D. et al., The development of species-specific immunodiagnostics for Stachybotrys chartarum: The role of cross-reactivity, Journal of Immunological Methods, 309: 150-159, 2006.

Chappelle, A. et al., Some Limitations in the Use of Urine Biomonitoring for Measuring TDI Exposure, 2001 (Abstract only).

\* cited by examiner

R' = Biomolecule 4,4 methylene diphenyl diisocyanate hexamethylene diisocyanate

| Chemical Name | Structure | Test Antigen (4µg/ml) | Optical density [405 nm, 30 min] | | | | | | | |
|---|---|---|---|---|---|---|---|---|---|---|
| | | | 2E5 | 60G2 | 62G5 | 79G7 | 64D2 | 32B6 | 59E5 | 16F4 |
| 2,4-toluene diisocyanate | 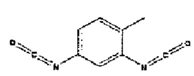 | 2,4-TDI-HSA | 4.15 | 4.08 | 4.01 | 3.9 | 0 | 4.12 | 0 | 2.4 |
| | | 2,4-TDI-KLH | 4.29 | 4.41 | 4.10 | 3.69 | 2.20 | 4.50 | 0 | 4.13 |
| | | 2,4-TDI-MSA | 4.43 | 4.30 | 4.40 | 4.30 | 0.80 | 4.20 | 0 | 3.40 |
| | | 2,4-TDI-keratin | 4.21 | 4.20 | 4.00 | 3.91 | 0 | 3.65 | 0 | 0 |
| | | 2,4-TDI-lysozyme | 0 | 1.65 | 1.0 | 2.00 | 0 | 0 | 0 | 0 |
| 2,6-toluene diisocyanate | 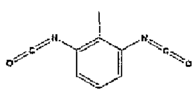 | 2,6-TDI-HSA | 0 | 4.16 | 4.21 | 4.28 | 3.85 | 4.21 | 4.21 | 4.23 |
| | | 2,6-TDI-KLH | 0 | 4.31 | 4.25 | 4.3 | 0 | 4.2 | 0 | 4.10 |
| | | 2,6-TDI-MSA | 0 | 4.25 | 4.35 | 3.85 | 0.31 | 4.25 | 0.78 | 3.28 |
| | | 2,6-TDI-keratin | 0 | 4.10 | 4.08 | 3.62 | 0 | 3.82 | 3.20 | 0 |
| | | 2,6-TDI-lysozyme | 0 | 0.68 | 1.16 | 0 | 0 | 1.6 | 0 | 0 |
| | | 2,4 TDI-collagen | 0 | 0 | 1.75 | 0 | 0 | 0 | 0 | 0 |
| Gorilla Glue | | Polymeric MDI-HSA | 0 | 2.72 | 0 | 0 | 1.65 | 0 | 0 | 0 |
| 4,4-methylene diphenyl diisocyanate | 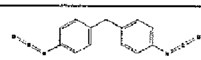 | MDI-HSA | 0 | 4.21 | 2.75 | 2.80 | 3.75 | 0.6 | 0 | 1.70 |
| 2,4;2,6 TDI | | 2,4;2,6 TDI-HSA | 3.85 | 3.81 | 3.83 | 4.06 | 0 | 4.10 | 3.44 | 3.26 |
| hexamethylene diisocyanate | 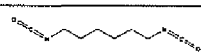 | HDI-HSA | 0 | 3.4 | 1.42 | 0 | 0 | 1.00 | 0 | 3.75 |
| 2,5-dimethyl phenylisocyanate | 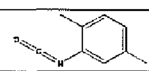 | 2,5-DMPI-HSA | 0 | 2.15 | 4.10 | 4.04 | 0 | 3.2 | 0 | 2.633 |
| 3,4-dimethyl phenylisocyanate | 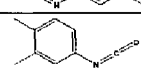 | 3,4-DMPI-HSA | 4.00 | 3.80 | 4.32 | 4.25 | 0 | 3.20 | 0 | 3.663 |
| 4-toluene isocyanate | 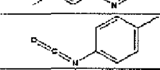 | PTI-HSA | 0 | 0 | 0 | 0 | 0 | 0 | 0 | 0 |
| 2-toluene isocyanate |  | OTI-HSA | 0 | 0 | 3.65 | 3.8 | 0 | 0 | 0 | 0 |
| phenyl isocyanate |  | PI-HSA | 0 | 0 | 0 | 0 | 0 | 0 | 0 | 0 |
| 2,4-toluene diisothiocyanate | 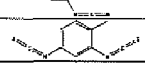 | 2,4-TITC-HSA | 0 | 0 | 0 | 0 | 0 | 0 | 0 | 0 |
| 2,6-toluene diisothiocyanate | 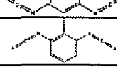 | 2,6-TITC-HSA | 0 | 0 | 0 | 0 | 0 | 0 | 0 | 0 |

FIGURE 6

| Chemical Name | Structure | Test Antigen (4µg/ml) | Dot blot scoring | | | | | | |
|---|---|---|---|---|---|---|---|---|---|
| | | | 2E5 | 60G2 | 62G5 | 79G7 | 32B6 | 59E5 | 16F4 |
| 2,4-toluene diisocyanate | | 2,4-TDI-HSA | +++ | +++ | +++ | +++ | +++ | 0 | +++ |
| | | 2,4-TDI-KLH | +++ | +++ | +++ | +++ | +++ | 0 | +++ |
| | | 2,4-TDI-MSA | +++ | +++ | +++ | +++ | +++ | 0 | +++ |
| | | 2,4-TDI-keratin | ++ | +++ | ++ | +++ | + | 0 | 0 |
| | | 2,4-TDI-collagen | | | | | | | |
| 2,6-toluene diisocyanate | | 2,6-TDI-HSA | 0 | +++ | +++ | ++ | +++ | +++ | +++ |
| | | 2,6-TDI-KLH | +++ | +++ | +++ | +++ | ++ | 0 | +++ |
| | | 2,6-TDI-MSA | 0 | ++ | +++ | ++ | +++ | + | +++ |
| | | 2,6-TDI-keratin | 0 | ++ | +++ | + | +++ | + | 0 |
| | | 2,6-TDI-lysozyme | 0 | 0 | 0 | 0 | 0 | 0 | 0 |
| | | 2,4 TDI-collagen | 0 | | | | | | |
| 4,4-methylene diphenyl diisocyanate | 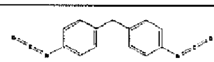 | MDI-HSA | 0 | ++ | + | 0 | 0 | 0 | + |
| 2,4;2,6 TDI | | 2,4;2,6 TDI-HSA | +++ | +++ | +++ | +++ | +++ | + | ++ |
| hexamethylene diisocyanate | 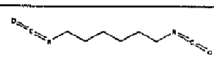 | HDI-HSA | 0 | + | 0 | + | 0 | 0 | + |
| 2,5-dimethyl phenylisocyanate | 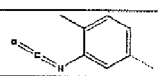 | 2,5-DMPI-HSA | 0 | + | +++ | +++ | + | 0 | ++ |
| 3,4-dimethyl phenylisocyanate | 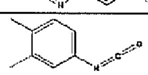 | 3,4-DMPI-HSA | 0 | + | +++ | +++ | + | 0 | ++ |
| 4-toluene isocyanate | 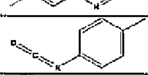 | PTI-HSA | 0 | 0 | 0 | 0 | 0 | 0 | 0 |
| 2-toluene isocyanate |  | OTI-HSA | 0 | 0 | +++ | ++ | 0 | 0 | 0 |
| phenyl isocyanate | 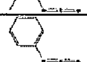 | PI-HSA | 0 | 0 | 0 | 0 | 0 | 0 | 0 |
| 2,4-toluene diisocyanate | | 2,4-TITC-HSA | 0 | 0 | 0 | 0 | 0 | 0 | 0 |
| 2,6-toluene diisocyanate | | 2,6-TITC-HSA | 0 | 0 | 0 | 0 | 0 | 0 | 0 |

METHODS AND COMPOSITIONS RELATING TO ISOCYANATE CONJUGATES

GOVERNMENT SPONSORSHIP

This invention was made by the Centers for Disease Control and Prevention, an agency of the United States Government. This invention was funded in part by NIEHS-NIOSH interagency agreement #Y1-ES-0001.

REFERENCE TO RELATED APPLICATION

This application claims priority from U.S. Provisional Patent Application Ser. No. 61/104,429, filed Oct. 10, 2008, the entire content of which is incorporated herein by reference.

FIELD OF THE INVENTION

The present invention relates generally to compositions and methods for the isolation, detection and/or quantification of diisocyanate-protein conjugates. In particular embodiments, the present invention relates to methods and compositions including monoclonal antibodies for specific recognition of 2,4-toluene diisocyanate; 2,6-toluene diisocyanate, methylene diphenyl diisocyanate and/or hexamethylene diisocyanate moieties of protein conjugates.

BACKGROUND OF THE INVENTION

Over 200,000 workers are directly employed in the production and use of diisocyanates, worldwide. Potential exposures to diisocyanates occur in virtually all aspects of our lives from agriculture to transport to leisure. They are commonly used in paints, glues/binders and foams.

Diisocyanates (dNCOs) are used in the production of polyurethanes such as polyurethane foams, elastomers and coatings[13]. Monoisocyanates (one N=C=O/molecule) are used in nonpolymer applications such as the production of insecticides, pesticides and herbicides[14]. The most widely used compounds are diisocyanates, which contain two isocyanate groups, and polyisocyanates, which are usually derived from diisocyanates and may contain several isocyanate groups. The most common monomeric dNCOs are toluene diisocyanate (TDI), methylene diphenyl diisocyanate (MDI) and hexamethylene diisocyanate (HDI). Others include naphthalene diisocyanate (NDI), methylene bis-cyclohexylisocyanate (HMDI) (hydrogenated MDI), and isophorone diisocyanate (IPDI). Examples of widely used polyisocyanates include HDI biuret and HDI isocyanurate.

Toluene diisocyanates are reactive intermediates often used to form urethane links. For example, toluene diisocyanates are used in combination with polyether and polyester polyols to produce polyurethane products. TDI is available in commercial preparations which often include an 80:20 mixture of 2,4-TDI and 2,6-TDI[15].

Workers are exposed to monomeric and polymeric forms of diisocyanates. The main route of exposure to dNCOs is through inhalation. Other common routes of exposure include eye contamination and skin contamination[16].

Responses to dNCOs exposure vary widely from mild irritation of the airways to more severe effects, including bronchospasm. Isocyanates are powerful irritants to the mucous membranes of the eyes, gastrointestinal tract and respiratory system[17]. Direct skin contact can cause marked dermal inflammation.

Respiratory effects are a primary toxicological manifestation of repeated exposure to diisocyanates[16]. Exposure to dNCOs are the most commonly reported cause of occupational asthma[1].

Diisocyanates can also sensitize workers, making them subject to allergic rhinitis, allergic contact dermatitis and asthma attacks upon re-exposure. Death from severe asthma in sensitized subjects has been reported[1].

Due to their widespread use in the general population particularly from products commercially available at hardware stores actual rates of dNCO induced diseases may be underreported. Health aspects of diisocyanates exposure have been subjected to intensive research, in terms of both human and animal toxicological studies. Dose-dependent responses to higher levels of dNCOs include respiratory, dermal and mucous membrane irritation. Hypersensitivity reactions to dNCO's include allergic rhinitis, asthma, hypersensitivity pneumonitis and allergic contact dermatitis.

Diisocyanates can bind to proteins through a number of chemical functional groups and the nature of this binding may depend on the protein and the local environment. FIG. 1 illustrates reactions of isocyanates with a biomolecule, such as protein, to form conjugates.

Conjugation (haptenation) of diisocyanate to human proteins after exposure is commonly accepted as an important primary event in the development of diisocyanate-induced allergic sensitization and asthma. Diisocyanates have been shown to bind to skin and lung resident proteins. The major adducts found in the blood are conjugates to hemoglobin and albumin[5]. TDI-conjugated lung proteins were co-localized with keratin, tubulin, laminin and actin[2-11, 19]. It is believed, that TDI binding, in vivo, demonstrates selectivity with respect to the target proteins. Detection of dNCO exposure and diagnosis of related pathological conditions is difficult. For example, detection of dNCO exposure-induced antibodies against dNCO in a subject is challenging and is typically attempted using poorly characterized haptenated albumin.

While asthma is considered an inflammatory disorder of the conducting airways, it is becoming increasingly apparent that the disease is heterogeneous with respect to immunopathology[17]. TDI-specific IgE can be detected in only about 20% of the TDI-asthmatics, suggesting that immunological pathways other than Type I allergic mechanisms, may predominate in the majority of the asthmatics. Although the role of specific IgE antibody has been investigated, the results thus far point to discrepancies or rather low associations between specific IgE antibodies and disease[24-28].

The contribution of using inappropriate antigen to the lack of specific-IgE detection in dNCO asthmatics is not known, but most studies evaluating different haptenated protein preparations, usually find differences in affinities of anti-TDI IgEs, but rarely identify a significant increase in TDI specific-IgE prevalence in TDI asthmatics.

The short circulating half-life of unbound serum IgE of about 2 days may be of unique importance to occupational illnesses such as isocyanate asthma. Brief periods away from the workplace may result in a decrease in serum IgE levels to levels undetected by conventional methods[29]. Without accurate exposure information, negative isocyanate-specific IgE assays may lead to misdiagnosis and false conclusions about pathogenic mechanisms.

TDI specific IgG antibodies have been found in subjects[11, 24, 26, 30-32], TDI specific-IgG has been documented as a marker of exposure rather than of disease[8]. The presence of dNCO specific-IgE and -IgG have been widely investigated as diagnostic markers of occupational asthma in diisocyanate-exposed workers[11, 21, 24, 29, 33-37].

Since effective assays are currently unavailable, a presumptive diagnosis of dNCO asthma is made from work history, report of work-related asthma-like symptoms and nonspecific airway reactivity to methacholine challenge.

In addition to asthma, irritant contact dermatitis (ICD) and allergic contact dermatitis (ACD) can be produced by dermal exposure to dNCOs. Irritant contact dermatitis is the most common form of chemical induced dermatitis. It is a dose-dependent toxic/non-immunologically mediated effect associated with a chemical's ability to react with skin components and damage the skin. Allergic contact dermatitis is a T-lymphocyte mediated delayed (Type IV, DTH) hypersensitivity/immunological reaction.

Diagnosis of DTH is usually confirmed by clinical dermal patch testing. Currently there are three widely used standardized patch test: 1) Finn chamber, 2) True test and 3) Epiquick[38]. In these tests, the suspected sensitizing agent is dissolved/suspended in a solvent (usually petrolatum). A patch containing the diluted agent is applied, occluded onto skin, and read at 48, 72 and 96 hours. A patch test is interpreted based on observation of redness, itching and induration of skin at the site of the patch[38, 39].

Biomonitoring of dNCOs involves either the measurement of specific antibody or of dNCO-conjugated biomolecules in blood or urine samples. Biomonitoring assays estimate total TDI exposure by converting TDI and its urinary metabolites to toluene diamine (TDA) by acid or base hydrolysis. A variety of analytical methods (e.g. chromatography) are used to determine the amount of TDA generated by laboratory hydrolysis[40, 41]. The detection of TDA in urine samples does not reflect the level of free TDA in the body, rather it estimates the combination of conjugated TDI derivatives and free-TDA[42, 42, 43]. This method does not distinguish between TDI and TDA exposure. Sabbioni et al. reported a dNCO biomarker assay employing mild base hydrolysis of hemoglobin from methylene diphenyl diisocyanate (MDI) exposed rats to yield the hydantoin from the MDI conjugated lysine of the N-terminal valine[44].

There is a continuing need for compositions, such as monoclonal antibodies, and methods using the compositions, to isolate and characterize dNCO-conjugated proteins from dNCO-exposed humans and non-human animals. Compositions and methods are needed for use in detection of dNCO-exposure and related disease conditions in humans and non-human animals.

SUMMARY OF THE INVENTION

Compositions are provided according to embodiments of the present invention which include an isolated antibody or antigen binding antibody fragment characterized by binding specificity for a conjugate which is a reaction product of a protein moiety and an isocyanate moiety.

The isocyanate moiety can be an aromatic or aliphatic isocayanate moiety.

In particular embodiments, compositions are provided according to embodiments of the present invention which include an isolated monoclonal antibody or antigen binding antibody fragment characterized by binding specificity for a conjugate which is a reaction product of a protein moiety and an diisocyanate moiety. The diisocyanate moiety can be an aromatic or aliphatic diisocayanate moiety.

A preferred aromatic diisocyanate moiety is a toluene diisocyanate. Toluene diisocyanates include, but are not limited to, 2,4-toluene diisocyanate and 2,6-toluene diisocyanate. Additional preferred diisocyanate moieties are methylene diphenyl diisocyanate and hexamethylene diisocyanate.

Compositions according to embodiments of the present invention include an isolated antibody or antigen binding antibody fragment characterized by binding specificity for a conjugate which is a reaction product of a protein moiety and an isocyanate moiety, wherein the binding specificity for the conjugate is independent of the identity of the protein moiety.

Methods of detecting diisocyanate-protein conjugates in a sample are provided according to embodiments of the present invention which include contacting a sample with a first isolated antibody or antigen binding antibody fragment characterized by binding specificity for a first diisocyanate-protein conjugate. Binding of the first antibody or antigen binding antibody fragment with the first diisocyanate-protein conjugate is then detected. In preferred embodiments, the first antibody is a monoclonal antibody or antigen binding fragment thereof.

In particular embodiments, methods of the present invention further include contacting a sample with a second isolated antibody or antigen binding antibody fragment characterized by binding specificity for a second diisocyanate-protein conjugate. Binding of the second antibody or antigen binding antibody fragment with the second diisocyanate-protein conjugate is then detected. In preferred embodiments, the second antibody is a monoclonal antibody or antigen binding fragment thereof.

A sample assayed for presence of one or more diisocyanate-protein conjugates is obtained from an individual mammalian subject, particularly a human subject in certain embodiments. Alternatively, the sample is an environmental sample.

One or more controls can be included in an assay according to embodiments of the present invention. For example, a positive control containing one or more diisocyanate-protein conjugates and/or known amounts of one or more diisocyanate-protein conjugates can be used. In a further example, a negative control, free of diisocyanate-protein conjugates can be used.

Kits for detection of diisocyanate-protein conjugates in a sample are provided according to embodiments of the present invention which include an isolated antibody or antigen binding antibody fragment characterized by binding specificity for a diisocyanate-protein conjugate wherein the binding specificity for the conjugate is independent of the identity of the protein moiety.

In further embodiments, provided kits include at least two isolated antibodies and/or antigen binding antibody fragments characterized by binding specificity for at least two diisocyanate-protein conjugates where the at least two diisocyanate-protein conjugates contain different diisocyanate moieties. Optionally, inventive kits contain at least three isolated antibodies and/or antigen binding antibody fragments characterized by binding specificity for at least three diisocyanate-protein conjugates where the at least three diisocyanate-protein conjugates contain different diisocyanate moieties. In preferred embodiments, the one or more antibodies included in kits of the present invention is a monoclonal antibody or antigen binding fragment thereof.

Where two or more antibodies or antigen binding antibody fragments are included in a kit, they can be provided as a mixture or separately.

BRIEF DESCRIPTION OF THE DRAWINGS

FIG. 6 is a table showing results of ELISA analysis of 9 monoclonal antibodies raised against diisocyanate-conjugated proteins;

FIG. 7 is a table showing results of dot blot analysis of monoclonal antibodies raised against diisocyanate-conjugated proteins;

FIG. 8A shows a dot blot analysis of a monoclonal antibody raised against a diisocyanate-conjugated protein; and FIG. 8B shows a dot blot analysis of a monoclonal antibody raised against a diisocyanate-conjugated protein.

DETAILED DESCRIPTION OF THE INVENTION

Figure 1:
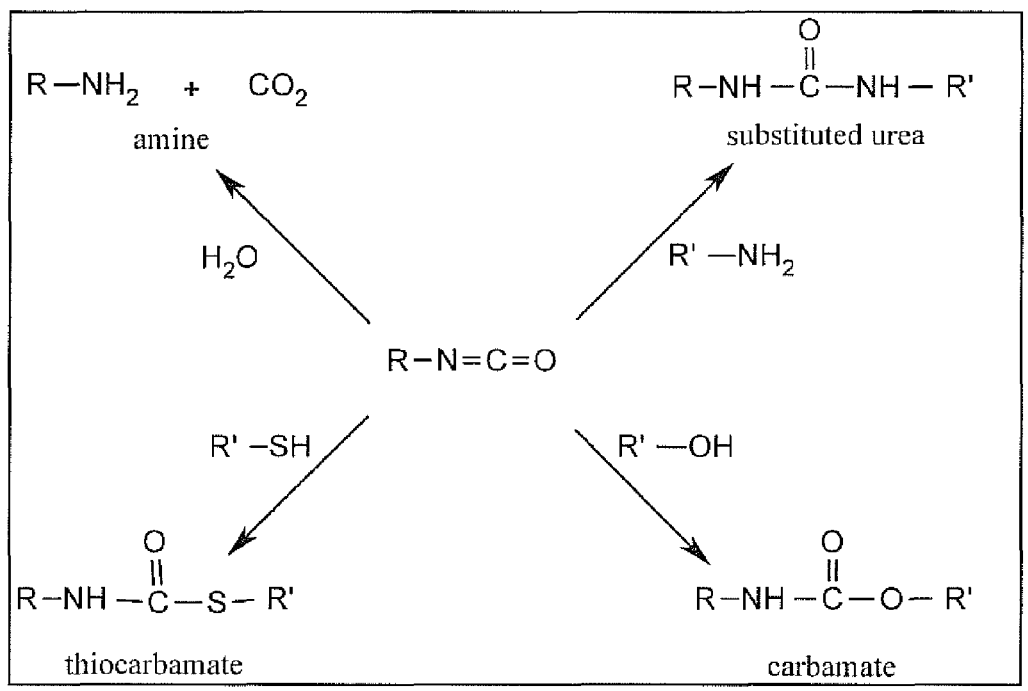
FIG. 1 illustrates certain reactions of isocyanates, including diisocyanates, with a biomolecule, such as protein, to form conjugates.

Monoclonal antibodies and fragments thereof that recognize an aliphatic diisocyanate or an aromatic diisocyanate conjugated to a biomolecule are provided according to embodiments of the present invention.

The term "biomolecule" refers to any component of a biological organism, illustratively including protein, carbohydrate, lipid and nucleic acid. In preferred embodiments, the term biomolecule refers to protein.

Monoclonal antibodies and fragments thereof that recognize TDI-bound proteins are provided according to embodiments of the present invention. In particular embodiments, monoclonal antibodies and fragments thereof are provided that selectively recognize 2,4-TDI-protein conjugates, 2,6-TDI-protein conjugates or both 2,4-TDI-protein conjugates and 2, 6-TDI-protein conjugates.

Monoclonal antibodies and fragments thereof according to embodiments of the present invention selectively recognize methylene diphenyl diisocyanate-protein conjugates or hexamethylene diisocyanate-protein conjugates.

Particular antibodies according to embodiments of the present invention recognize more than one TDI moiety of TDI-conjugates. Monoclonal antibodies and fragments thereof according to the present invention are specific for a diisocyanate-protein conjugate where the conjugate is a reaction product of a protein moiety and a diisocyanate moiety.

In preferred embodiments, the specificity of the antibody or antibody fragment for a conjugate is independent of the identity of the protein moiety. In certain embodiments, monoclonal antibodies and fragments thereof are provided that specifically recognize dNCO bound to a protein through a particular linkage, such as urea, urethane, carbamate or thiocarbamate linkage.

Monoclonal antibodies and fragments thereof provided according to the present invention have utility in numerous applications, including, but not limited to, diagnosis, immunohistochemistry and biomarker immunoassays of dNCO exposure. In addition, they are useful for identifying and quantifying dNCO-bound proteins.

For example, specific dNCO-bound proteins are identified following exposure of a subject to dNCOs, including exposure by various routes such as dermal and inhalation exposures.

Particular terms used in describing the present invention are well-known terms of molecular biology, cell biology, immunology and the like. Such terms are described in detail in standard texts such as E. Harlow and D. Lane, Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; B. K. C. Lo, Antibody Engineering: Methods and Protocols, Methods in Molecular Biology, Humana Press, 2003; F. M. Ausubel et al., Eds., Short Protocols in Molecular Biology, Current Protocols, Wiley, 2002; and J. Sambrook; Crowther, J. R., The ELISA Guidebook (Methods in Molecular Biology), Humana Press, 2000; Wild, D., The Immunoassay Handbook, 3rd Edition, Elsevier Science, 2005; and D. W. Russell, Molecular Cloning: A Laboratory Manual, Cold Spring Harbor Laboratory Press, 3rd Ed., 2001.

As used herein, the terms "antibody" and "antibodies" relate to monoclonal antibodies, polyclonal antibodies, bispecific antibodies, multispecific antibodies, humanized antibodies, chimeric antibodies, camelized antibodies, single domain antibodies, single-chain Fvs (scFv), single chain antibodies, disulfide-linked Fvs (sdFv), and anti-idiotypic (anti-Id) antibodies (including, e.g., anti-Id antibodies to antibodies of the invention), and epitope-binding fragments of any of the above. In particular, antibodies include immunoglobulin molecules and immunologically active fragments of immunoglobulin molecules, i.e., molecules that contain an antigen binding site. Immunoglobulin molecules are of any isotype (e.g., $IgG_1$, $IgG_{2a}$, $IgG_{2b}$, $IgG_3$, $IgG_4$, $IgA_1$, $IgA_2$, IgM, IgD, IgE, and IgY).

Antibodies can be made in any animal and/or in cells derived from any animal which produces antibodies specific for a diisocyanate-protein conjugate, including mammals and non-mammals. For example, antibodies of the present invention can be rodent antibodies such as mouse antibodies or rat antibodies. Optionally, antibodies are chemically synthesized or generated using recombinant techniques including phage display.

In preferred embodiments, antibodies according to the present invention are monoclonal antibodies or antigen binding fragments of monoclonal antibodies.

In preferred embodiments, mouse monoclonal IgG and IgM antibodies are produced and the mouse monoclonal antibodies and/or antigen binding fragments thereof are used in assays according to the present invention.

As used herein, the term "antigen binding antibody fragment" defines a fragment of an antibody that specifically binds to a diisocyanate moiety-protein conjugate. Antigen binding antibody fragments illustratively include an Fab fragment, an Fab' fragment, an F(ab')2 fragment, an Fd fragment, an Fv fragment, an scFv fragment and a domain antibody (dAb), for example. Antibody fragments may be generated by any technique known to one of skill in the art. For example, Fab and $F(ab)_2$ fragments may be produced by proteolytic cleavage of immunoglobulin molecules, using enzymes such as papain (to produce Fab fragments) or pepsin (to produce $F(ab)_2$ fragments). $F(ab)_2$ fragments contain the complete light chain, and the variable region, the CH1 region and the hinge region of the heavy chain. Antigen binding antibody fragments are also produced by recombinant DNA technologies. Antigen binding antibody fragments may be one or more complementary determining regions (CDRs) of antibodies.

In particular embodiments, antibodies of the present invention are generated using a dNCO conjugated to a non-mammalian protein or peptide as an antigen. Antibodies generated against the antigen are screened to determine reactivity with one or more dNCO-conjugated mammalian proteins. In preferred embodiments, selected antibodies are characterized by binding specificity for dNCO-conjugated proteins and do not show binding specificity to protein alone.

The term "binding specificity" when referring to an antibody or antigen binding antibody fragment is well-known in the art and methods for characterizing an antibody or antigen binding antibody fragment for its binding specificity are also well-known.

An antibody which is characterized by binding specificity for a particular antigen generally has a dissociation constant, Kd, less than about $10^{-6}$ M, such as less than about $10^{-7}$ M, less than about $10^{-8}$ M, less than about $10^{-9}$ M, less than about $10^{-10}$ M or less than about $10^{-11}$ M, or less depending on the specific composition. Binding affinity of an antibody can be determined by Scatchard analysis such as described in P. J. Munson and D. Rodbard, Anal. Biochem., 107:220-239, 1980.

It is appreciated that an antibody or antigen binding antibody fragment characterized by binding specificity for a particular antigen does not necessarily exclusively bind only to that particular antigen but may also bind to one or more additional antigens with lower affinity and/or avidity.

Methods of generating antibodies and antigen binding antibody fragments are well-known in the art as detailed in standard texts such as E. Harlow and D. Lane, Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; and B. K. C. Lo, Antibody Engineering: Methods and Protocols, Methods in Molecular Biology, Humana Press, 2003.

Generation of monoclonal antibodies is well-known in the art and includes generation by hybridoma methodology, recombinant generation, phage selection as well as other techniques. Such methodology is detailed in standard texts such as Kohler, G et al, Nature, 256:495-497, 1975; E. Harlow and D. Lane, Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; and B. K. C. Lo, Antibody Engineering: Methods and Protocols, Methods in Molecular Biology, Humana Press, 2003.

The term "isolated" as used herein refers to a substance that has been separated from contaminating cellular components or other materials not intended to be associated with the substance and that would interfere with use of the substance in assays or other uses. An "isolated" substance may be, but is not necessarily, pure. Generally, an isolated substance described herein is at least about 80% pure, at least about 90% pure, at least about 95% pure, or greater than about 99% pure. Purification is achieved using well-known standard methodology such as fractionation and/or chromatography, such as ammonium sulfate precipitation and elution chromatography such as size exclusion chromatography, displacement chromatography, ion exchange chromatography and bioaffinity chromatography. Exemplary purification methodology is described in S. Doonan, Protein Purification Protocols Humana Press, 1996 and herein.

Assays

A method of detecting a conjugate in a sample according to embodiments of the present invention includes contacting the sample with an antibody or antibody fragment having binding specificity for an aliphatic or aromatic diisocyanate moiety. Binding of the antibody or antibody fragment with the aliphatic or aromatic diisocyanate moiety is detected, thereby detecting the aliphatic or aromatic diisocyanate moiety in the sample.

In particular embodiments, the aliphatic or aromatic diisocyanate moiety detected is part of a conjugate containing an aliphatic or aromatic diisocyanate moiety bound to a protein.

A method of detecting a conjugate in a sample according to embodiments of the present invention includes contacting the sample with an antibody or antibody fragment having binding specificity for a conjugate which is the reaction product of a protein moiety and a diisocyanate moiety, the reaction fanning a modified protein and a modified diisocyanate in urea, urethane, carbamate or thiocarbamate linkage with each other. Binding of the antibody or antibody fragment with the conjugate is detected, thereby detecting the conjugate in the sample.

Any sample can be assayed for diisocyanate-protein conjugates using antibodies or antigen binding antibody fragments of the present invention. A sample assayed for diisocyanate-protein conjugates is an environmental or biological sample in embodiments of the present invention.

For example, a biological sample can be a material obtained from an individual subject, such as a fluid or tissue sample illustratively including, blood, plasma, serum, cerebrospinal fluid, tears, saliva, urine, milk, lymph, ascites, lung exudate, nasopharyngeal secretions and gastric fluid. An individual subject can be any human or non-human animal, particularly mammals. In certain embodiments, an individual subject is a human.

An assay for detection of 2,4-toluene diisocyanate-protein conjugates, 2,6-toluene diisocyanate-protein conjugates, methylene diphenyl diisocyanate-protein conjugates and hexamethylene diisocyanate-protein conjugates includes contacting a sample with an antibody of the present invention which is specific for one or more of the conjugates and detecting the binding of the antibody or antigen binding antibody fragment and conjugate.

Detecting the formation of a complex between anti-diisocyanate moiety-protein conjugate antibodies and fragments thereof present in a biological sample and a diisocyanate moiety-protein conjugate is achieved by any of various methods known in the art, illustratively including detection of a label attached to a diisocyanate moiety-protein conjugate or attached to the anti-diisocyanate moiety-protein conjugate antibodies or fragments thereof. The term "label" or "labeled" refers to any composition which can be used to detect, qualitatively or quantitatively, a substance attached to the label by any appropriate method illustratively including spectroscopic, optical, photochemical, biochemical, enzymatic, electrical and/or immunochemical. Examples of suitable labels include a fluorescent moiety, a radioisotope, a chromophore, a bioluminescent moiety, an enzyme, a magnetic particle, an electron dense particle, a nanoparticle, a nucleic acid molecule and the like. The term "label" or "labeled" is intended to encompass direct labeling of a diisocyanate moiety-protein conjugate or an antibody by coupling (i.e., physically linking) a detectable substance to the diisocyanate moiety-protein conjugate, antibody or antigen binding antibody fragment, as well as indirect labeling of the diisocyanate moiety-protein conjugate, antibody or antigen binding antibody fragment by interaction with another reagent that is directly labeled. An example of indirect labeling of a primary antibody includes detection of a primary antibody using a fluorescently labeled secondary antibody.

Labels used in detection of complex formation depend on the detection process used. Such detection processes are incorporated in particular assay formats illustratively including ELISA, dot blot, western blot, immunoprecipitation, immunocytochemistry, immuno-fluorescence assay, liquid chromatography, flow cytometry, other detection processes known in the art, or combinations thereof.

Commercial mixtures usually contain 80/20 or 60/40 mixtures of 2,4-TDI/2,6-TDI, but actual occupational exposures may vary as reactivity and volatilities of the isomers are different. It is appreciated that an assay of the present invention is operative to determine the amount of or isolate of a particular conjugate.

Compositions and methods of the present invention have utility in assays for detecting exposure of an individual to dNCOs. dNCO-protein conjugates may be measured from a person's blood, tissue or urine as biomarkers of exposure. Monoclonal antibodies and antigen binding antibody fragments thereof according to the present invention can be used for immunohistochemical staining from exposed humans or animals, such as of nasal epithelium of a scraping in particular embodiments.

In particular embodiments, monoclonal antibodies and antigen binding antibody fragments thereof according to the present invention can be used to assay dNCO air levels by using a sampler containing a protein to trap the dNCO from the air and then measure the dNCO-protein amount with the antibody or fragment.

In further embodiments, monoclonal antibodies or antigen binding antibody fragments thereof according to the present invention can be used to isolate dNCO-protein conjugates in a sample in order to identify the protein component of the conjugates. For example, following isolation of dNCO-protein conjugates from a sample using monoclonal antibodies or fragments thereof, the protein component of the isolated conjugates can be further characterized or identified by immunoassays or spectroscopic techniques and the like.

Assays according to embodiments of the present invention include contacting a sample with at least one antibody or antigen binding antibody fragment characterized by binding specificity for a first dNCO-protein conjugate and detecting binding of the antibody or antigen binding antibody fragment with the first conjugate.

In further embodiments, methods of the present invention include contacting the sample with at least a second antibody or antigen binding antibody fragment characterized by binding specificity for a second dNCO-protein conjugate and detecting binding of the antibody or antigen binding antibody fragment with the second conjugate.

In still further embodiments, methods of the present invention include contacting the sample with at least 3, 4, 5, 6 or more antibodies and/or antigen binding antibody fragments characterized by binding specificity for a $3^{rd}$, $4^{th}$, $5^{th}$, $6^{th}$ or additional dNCO-protein conjugates and detecting binding of the antibodies or antigen binding antibody fragments with the $3^{rd}$, $4^{th}$, $5^{th}$, $6^{th}$ or additional conjugates.

Multiple antibodies and/or antigen binding antibody fragments can be contacted with a single sample. In other embodiments, multiple samples from a single subject or portions of a single sample are obtained and contacted with each of the two or more antibodies or antigen binding antibody fragments separately, such as in separate wells of a multi-well container.

Kits

Kits including at least one antibody and/or antigen binding antibody fragment characterized by binding specificity for a dNCO-protein conjugate are provided according to embodiments of the present invention.

Kits including a panel of antibodies and/or antigen binding antibody fragments are provided according to embodiments of the present invention which include at least two antibodies and/or antigen binding antibody fragments characterized by binding specificity for at least two dNCO-protein conjugates where the at least two dNCO-protein conjugates contain different dNCO moieties.

In particular embodiments, kits including a panel of antibodies and/or antigen binding antibody fragments are provided according to embodiments of the present invention which include at least two antibodies and/or antigen binding antibody fragments characterized by binding specificity for at least two dNCO-protein conjugates selected from a 2,4-toluene diisocyanate-protein conjugate; a 2,6-toluene diisocyanate-protein conjugate; a methylene diphenyl diisocyanate-protein conjugate and a hexamethylene diisocyanate-protein conjugate.

Kits of the present invention may further contain any materials useful in performing assays using inventive antibodies. Reagents illustratively including buffers, secondary antibodies or detectable labels can also be included in inventive kits. Containers for performing assays are optionally included. Instructions for use and interpretation of results may also be provided in an inventive kit.

Embodiments of inventive compositions and methods are illustrated in the following examples. These examples are provided for illustrative purposes and are not considered limitations on the scope of inventive compositions and methods.

EXAMPLES

Example

Conjugation

Keyhole limpet hemocyanin (KLH, Hemocyanin from Megathura crenulata), mouse serum albumin (MSA, fraction V), human serum albumin (HSA, fraction V), lysozyme (chicken egg white), keratin protein (derived from hair, wool, horn, nails or other similar tissues in animals), and collagen (calf skin type 1 species) are obtained from Sigma Aldrich (St. Louis, Mo.). Dimethy phenyl isocyanates (DMPI) (2,3 DMPI, 3,5 DMPI and 2,5 DMPI) are obtained from Alfa Aesar (Wade Hill Mass.). 2,4 toluene diisocyanate (2,4 TDI), 2,6 toluene diisocyanate (2,6 TDI), hexamethylene diisocyanate (HDI), o-toluene isocyanate (OTT), p-toluene isocyanate (PTI), toluene diisothiocyanate phenyl isocyanates (2,4 TITC and 2,6 TITC) and methylene bis-cyclohexylisocyanate (MDI) are obtained from Sigma Aldrich (St. Louis, Mo.).

Figure 2A:
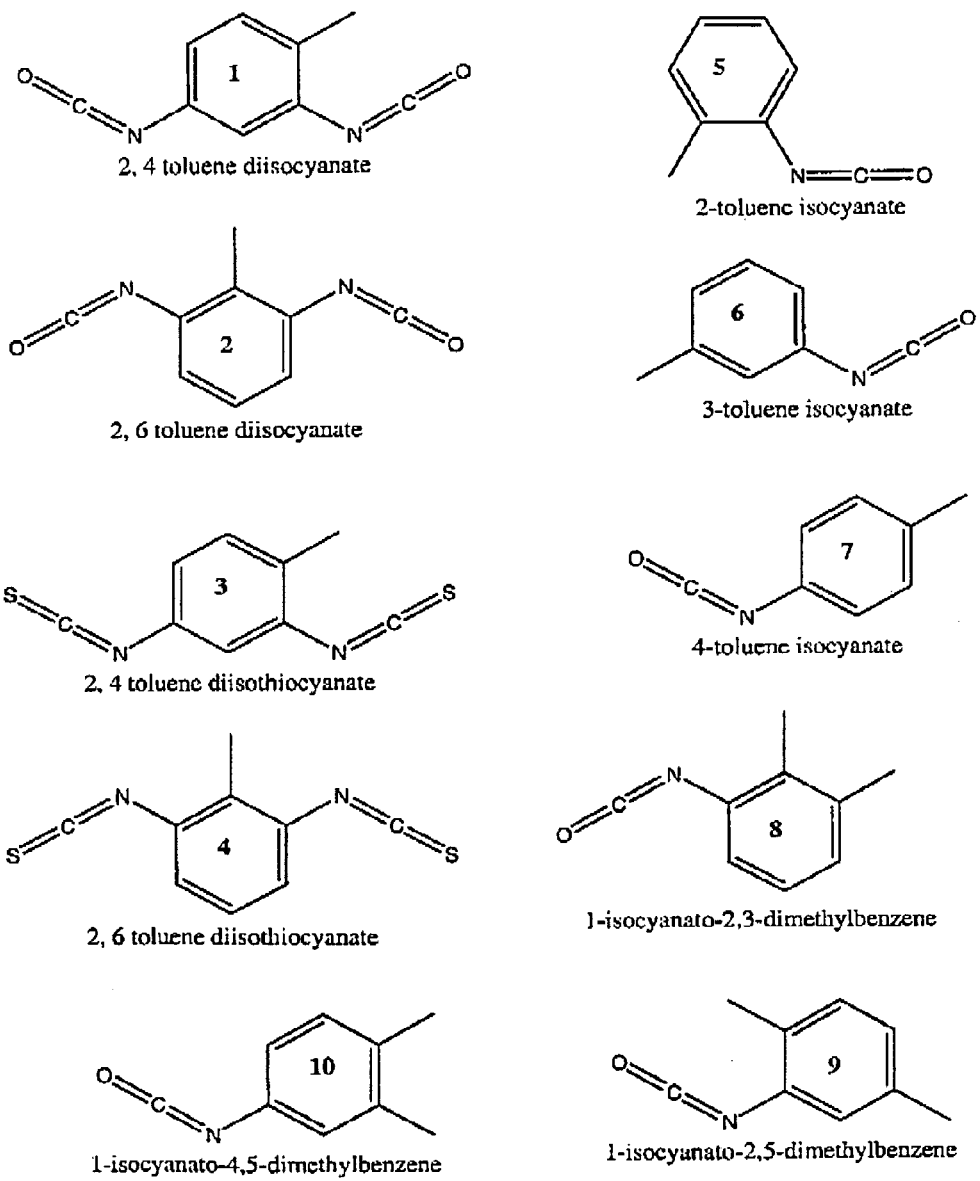
FIG. 2A shows isocyanate and diisocyanate structures.
Figure 2B:
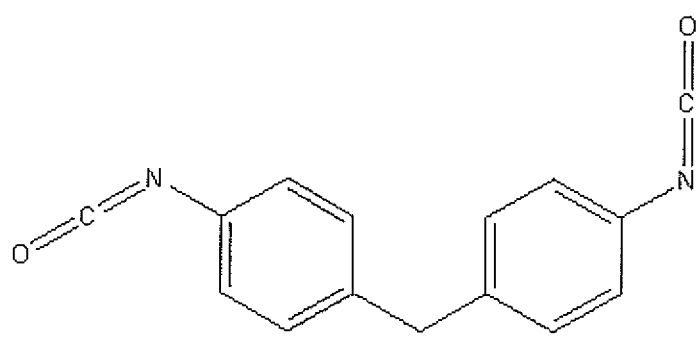
FIG. 2B shows MDI and HDI structures.
Figure 2B:
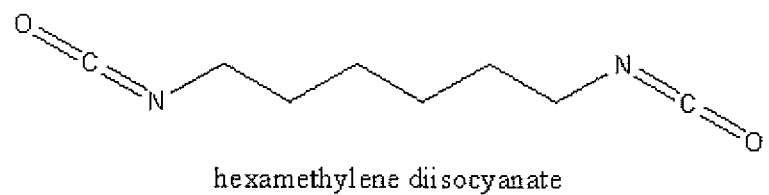

All proteins are dissolved or suspended to 5 mg/mL in phosphate buffed saline (PBS), pH 7.4. Five µl, aliquots of each dNCO, mono-isocyanate (NCO) or dithioisocyanate (dNCS) are added to 450 µL dry HPLC grade acetone (Sigma) and infused into the protein solution at a rate of 1.2 mL/hr at room temperature (RT) using a syringe pump (model 100; KD Scientific Inc., Holliston, Mass., USA), while rapidly stirring until a molar ratio of 1:40 protein:dNCO(NCO or dNCS) is achieved. The resulting conjugates are centrifuged at 300 g then dialyzed with 3× buffer changes in 1×PBS buffer at 4° C. using molecular porous membrane tubing obtained from Spectrum Laboratories, (Rancho Dominguez, Calif. MWCO:12-14 000, No 2). HSA is acylated with acetic anhydride to block all available primary amines prior to reaction with 2,4-TDI in a separate preparation. The conjugates are sterile filtered through 0.45 µm syringe filters (Millipore, Billerica, Mass., USA) and stored in aliquots at −20° C. FIGS. 2A and 2B illustrate the referenced compounds. The full list of conjugates is shown in Table 1.

Acetylation

Acetylation of HSA is done to block the amine binding site to prevent TDI reaction through an amide bond. The acetylation is performed as described Habeeb 1958[47]. Dialysis is used to separate the modified protein from other reaction products (acetic acid) and to transfer the protein into an appropriate physiological buffer.

Protein Quantification

The Bradford Protein assay is used to quantify the amount of protein after conjugations[50, 51]. The assayed protein concentrations are within the expected range of approximately 5 mg/mL, see Table I.

Conjugation Analysis

Chemical characterization of TDI haptenated proteins is a very difficult task as TDI can polymerize, and inter/intra cross-link protein sites. Several techniques are employed to evaluate the TDI conjugated proteins. These include:

(1) loss of primary amines from the protein as assessed by loss of reactivity to 2,4,6-trinitrobenzenesulphonic acid (TNBS)[52-54]. The isocyanates binding fraction is calculated as the percent of amino groups that had reacted with isocyanates according to Lemus et al[37] as follows:

$$\% S = 100 - \frac{[100 \times A^*]}{A} \quad \text{Equation 1}$$

where S is the substitution, $A^*$ is the Absorbance$_{420nm}$ of the isocyanate conjugate and A is the Absorbance$_{420nm}$ of the carrier protein.

(2) shift in average protein mass as assessed by Matrix Assisted Laser Desorption and Ionization-Time of Flight-Mass Spectrometry (MALDI-TOF-MS) and gel electrophoresis and (3) identification of specific binding sites following protein enzymatic digestion and analysis by High Performance Liquid Chromatographic-Quadrupole-Time of Flight Mass Spectrometry (HPLC-Q-TOF).

The extent of adduction of the conjugates is analyzed by 2 methods presented in Table I. Using TNBS conjugation is confirmed, however some of the conjugates give a negative TNBS assay result. The TNBS reagent assesses primarily chemical adduction with primary amines of amino acids[65] on the surface of the protein. Additional analyses are performed using mass spectrometry. For a molar ratio of 1:40 HSA:dNCO, the TNBS assay indicates 10 bound TDI adducts which is in agreement with the 11 amine residues available for binding on the surface of HSA, however mass spectrometry detected 23 adducts/HSA molecule. This difference may be caused by the dNCO reacting with nucleophilic groups other than amines and/or extensive cross linking and polymerization of the dNCO causing it to have a high number of conjugation adducts. Binding of one isocyanate to the protein and hydrolysis of the other on the dNCO will also result in no net change in the number of available primary amines and no decrease in TNBS absorbance. The chemical conjugates in Table I are also used for assessing monoclonal antibody binding specificity.

TABLE I

Characterization of protein adducts using spectroscopic procedures.

| Protein | Measured Concentration (mg/mL) | % Substitution (Using equation 1) | Number of bound Isocyanate by TNBS | Number of bound Isocyanate by Mass spectrometry |
|---|---|---|---|---|
| HSA | 5.7 | 0 | 0 | |
| HSA-2,4 TDI 1:40 | 4.4 | 87 | 10 | 23 |
| HSA-2,4 TDI 1:10 | 4.41 | 90 | 11 | |
| HSA-2,6 TDI 1:40 | 4.3 | 85 | 2 | 43 |
| HSA-2,6 TDI 1:10 | 3.7 | 69 | 9 | |
| HSA-2,4; 2,6 pure | 4.1 | 85 | 9 | — |
| HSA-2,4; 2,6 industrial | 4.5 | 82 | 9 | — |
| HSA-2,4 1st; 2,6 | 5.6 | 70 | 8 | 3 |
| HSA-2,6 1st; 2,4 | 5.4 | 61 | 5 | 3 |
| Collagen | 0.1 | 0 | — | 0 |
| Collagen-2,6 TDI | — | 61.8 | — | — |
| Collagen-2,4TDI | — | — | — | — |
| Keratin | — | 0 | — | — |
| Keratin-2,4 TDI | — | 71 | — | — |
| Keratin-2,6 TDI | — | 63 | — | — |
| Lysozyme | — | 0 | — | 0 |
| Lysozyme-2,4TDI | — | 87 | — | 3 |
| Lysozyme-2,6TDI | — | 87 | — | — |
| HSA-HDI | 4.5 | 77 | 8 | 26 |
| HSA-MDI | 5.0 | 66 | 7 | 25 |
| AcylHSA | 0.2 | — | — | — |
| AcylHSA-2,6 TDI | — | — | — | — |
| AcylHSA-2,4TDI | — | — | — | — |
| KLH | 6.1 | 0 | — | 0 |
| KLH-2,4TDI 1:40 | 5.2 | 84 | — | — |
| KLH-2,4TDI 1:10 | 5.6 | 77 | — | — |
| KLH-2,6TDI 1:40 | 5.2 | 84 | — | — |
| KLH-2,6TDI 1:10 | 5.9 | 84 | — | — |

TABLE I-continued

Characterization of protein adducts using spectroscopic procedures.

| Protein | Measured Concentration (mg/mL) | % Substitution (Using equation 1) | Number of bound Isocyanate by TNBS | Number of bound Isocyanate by Mass spectrometry |
|---|---|---|---|---|
| HSA-PTI 1:40 | 2.5 | 21 | 2 | 3 |
| HSA-PTI 1:10 | 4.2 | 12 | 1 | — |
| HSA-O-Toluene isocyanate (OTI) 1:40 | 3.1 | 40 | 4 | — |
| HSA-OTI 1:10 | 3.8 | 26 | 3 | — |
| HSA-Phenyl Isocyanate (PI) 1:10 | 4.0 | 10 | 1 | — |
| HSA-PI 1:40 | 3.0 | 14 | 2 | 5 |
| Mouse Serum Albumin (MSA)-2,4 TDI | 3.4 | 53 | — | 15 |
| MSA-2,6 TDI | 3.3 | 30 | — | 5 |
| HSA-2,4 toluene diisothiocyanate (TITC) | 3.4 | 39 | 4 | 4 |
| HSA-2,6 TITC | 2.6 | 37 | 4 | 2 |
| HSA-2.3 dimethyl phenyl isocyanate (DMPI) | 4.6 | 83 | 9 | 25 |
| HSA-2.5 DMPI | 3.1 | 81 | 9 | 27 |
| HSA-3.5 DMPI | 3.3 | 73 | 8 | 22 |

Figure 3:
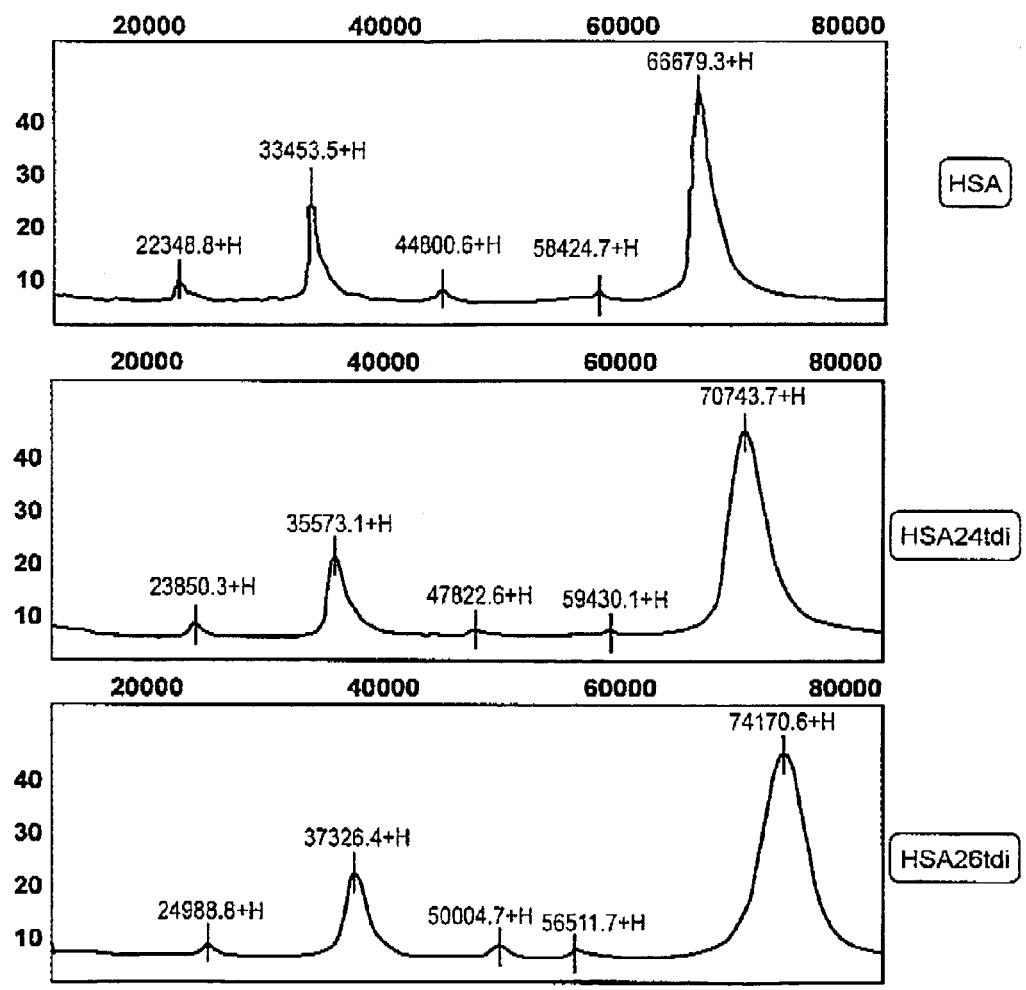
FIG. 3 shows representative mass spectra demonstrating dNCO conjugation to albumin.

The MALDI mass spectra in FIG. 3 show typical scans collected for the native protein and its conjugates. The determination of bound dNCOs is calculated by mass difference. The average molecular weight (MW) of HSA is 66679 amu. The average MW for 2,4-TDI-HSA is 70743 amu indicating an average of 23 dNCO moles/mole HSA, whilst that for 2,6-TDI-HSA indicates a 43 dNCO moles/mole HSA. Campo et al compared HDI conjugations from various groups using different conjugation techniques ranging from 0.3 to 33 dNCO/HSA and in this example there are 26 dNCO/HSA by mass spectrometry.

Figures 4A, 4B:
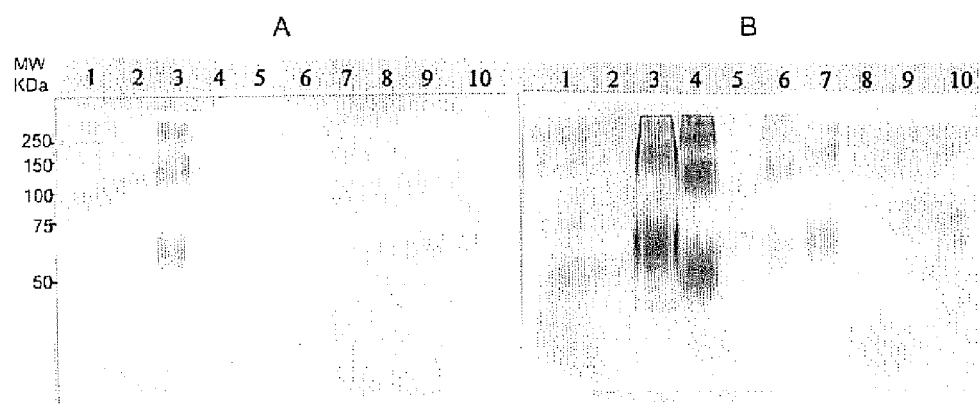
FIG. 4A shows a Western blot using a mAb of the present invention having binding specificity for a diisocyanate-protein conjugate.
FIG. 4B shows a Western blot using a mAb of the present invention having binding specificity for a diisocyanate-protein conjugate.

The spectra also suggest dimer formation as there also are peaks at around 120 000 amu, a fact also confirmed by immunoblots, see FIGS. 4A and 4B. This could be due to one dNCO crosslinking two molecules of HSA.

Example

Antibody Production

Female specific-pathogen-free inbred C57BL/6 mice are purchased from Jackson Laboratories (Bar Harbor, Me.) at 5 to 6 weeks of age. Upon arrival the mice are quarantined for 2 weeks and acclimated to a 12-hour light/dark cycle. Animals are housed in ventilated microisolator cages under environmentally controlled conditions at the NIOSH animal facility in compliance with AAALAC approved guidelines and an approved IACUC protocol. The animal rooms are monitored for specific pathogens through a disease surveillance and a sentinel animal program. Food and water are provided ad libitum.

Mice are immunized with 2,4-TDI, 2,6-TDI or MDI conjugated to the carrier protein Keyhole Limpet Hemocyanin (KLH) in a 50% TiterMax® adjuvant emulsion by intraperitoneal (IP) injection. Booster injections of the antigen in saline or TiterMax® are given biweekly and titers checked using blood drawn from the tail vein. This enhances production of antibodies directed against the TDI-protein complex. TDI-specific IgG titer (screened against TDI conjugated HSA) development is monitored by taking a pre-bleed from the tail vein prior to the first immunization and 7 days after each immunization. Approximately, 100 µl of blood is collected during each blood draw and several blood draws are conducted. The final boost is administered 3 days before the fusion. The animals are sacrificed by $CO_2$ asphyxiation and the spleen removed aseptically for hybridoma production.

Myeloma Cell Preparation

Cell viability of exponentially growing myeloma cells is checked microscopically prior to use. Myeloma cultures are split in half 12 h prior to the fusion to obtain mitotically active cells.

Fusion

Hybridomas are produced using standard polyethyleneglycol-based cell fusion techniques[66] using SP2/0-AG14 myelomas (ATCC#CRL-1581) at a ratio of 1:10 myeloma to spleen cells. Cell cultures are maintained in Dulbecco's Modified Eagle Medium (Life Technologies, Rockville, Md.), supplemented with 1 mM pyruvate, 100 units/mL penicillin, 100 µg/mL streptomycin and 0.292 mg/mL L-glutamine, 100 µM sodium hypoxanthine, 16 µM thymidine and 10% fetal calf serum (HyClone, Logan, Utah) and 100 units/mL IL-6 (Boehringer Mannheim, Germany).

Cloning

Culture supernatants from wells with cell growth are screened by ELISA (see below) and hybridomas from positive wells are cloned twice by limiting dilution. After 7 days, culture fluid is recovered from each well and screened for TDI-HSA-reactive IgG. All negative wells are discarded. Cells from positive wells are immediately re-cloned to prevent overgrowth by co-cultured nonsecreting hybrids. Stable hybridomas are bulk grown in culture plates and aliquots are stored in liquid nitrogen.

Freezing and Recovery of Hybridoma Cell Lines

Hybridoma cells are frozen in fetal calf serum containing 10% dimethyl sulfoxide, Vials are kept initially in a styrofoam box at −70° C.° for 7 days and then transferred to liquid nitrogen for long term storage The hybridomas are screened for TDI-HSA reactive antibodies. In order to avoid KLH specific mAbs and carrier protein dependent mAbs, TDI-HSA is selected as screening antigen for the hybridomas rather than TDI-KLH that is used for mouse immunization. Thus, any anti-TDI monoclonal antibodies produced are carrier protein independent.

Reactivity Studies

Reactivity studies are performed to determine the specificity of the epitopes recognized by the monoclonal antibodies. The various conjugates are used as solid-phase antigens in an alkaline-phosphatase-based indirect ELISA. An ELISA uses intact proteins. Western blot analysis is also used to investigate whether the monoclonal antibody can bind to denatured dNCO-conjugated proteins.

Antibody Isotype Determination and Quantification

Antibodies are isotyped using a mouse monoclonal isotyping kit. These kits contain secondary anti-mouse antibodies that are specific for all the mouse immunoglobulin isotypes i.e. $IgG_1$, $IgG2_a$, $IgG2_b$, $IgG_3$, IgM, IgA, IgD and IgE.

For mAb quantification, the amount of specific antibody in the supernatant is determined from a standard curve generated with isotype-matched antibodies of known concentrations. The standards and supernatant are then assayed in parallel.

ELISA

Hybridoma screening and cross-reactivity tests are performed by coating 96-well ELISA plate wells with the appropriate TDI-protein conjugate in carbonate coating buffer, pH 9.6 at room temperature (RT). Following overnight incubation and all subsequent ELISA steps, wells are washed 3× by incubating 200 µl of PBST (phosphate-buffered saline containing 0.05% Tween 20) per well for 5-min intervals. The plates are blocked by incubating for 1 h at RT in 200 µL of PBST containing 1% non-fat dry milk powder (PBSTM). Hybridoma culture supernatants are incubated for 1 h at 37° C. with 100 µl of mAb culture supernatant diluted 1 to 5 in PBSTM. Bound antibodies are labeled with 100 µL of Biotin-SP-conjugated AffiPure goat anti-mouse IgG secondary antibody (Jackson ImmunoResearch Laboratories, Inc., West Grove, Pa.) by incubation for 1 h at 37° C. at a dilution of 1/5000 in PBSTM. Bound biotin is detected with 100 µL of alkaline phosphatase-conjugated streptavidin (Jackson ImmunoResearch Laboratories) by incubation for 1 h at 37° C. at a dilution of 1/5000 in PBSTM. The extent of the reaction is revealed by incubating 100 µL per well of p-nitrophenyl phosphate-containing buffer [5 mg substrate in 10 ml of buffer (97 ml diethanolamine, 100 mg $MgCl_2$ diluted in 1 liter distilled water, pH 9.8)] at RT and the optical density (OD) is determined spectrophotometrically at 405 nm after a substrate incubation time of 30 min using an UltraMicroplate Reader, Model ELx800 (BIO-TEK Instruments, Inc., Winooski, Vt.).

Immunization for mAb Production

Five female BALB/c are immunized 4-6 times intraperitonially at biweekly intervals. Mice are primed and boosted with 50 µg of 2,4-TDI-KLH. Mice are immunized with 2,4-TDI-KLH at a 1:40 (KLH:dNCO) molar ratio emulsified in TiterMax®. In order to monitor titer development, tail vein bleeds are taken before immunization (pre-bleed) and 7 days following each immunization. The sera (polyclonal) antibodies are screened for reactivity to 2,4-TDI-HSA and their specificity is investigated by screening in parallel 2,6-TDI-HSA, 2,4- and 2,6-TDI-MSA and unconjugated HSA and MSA using the above ELISA.

TABLE II

Immunization Titers

| | 2,4 TDI-HSA | | | | 2,6 TDI-HSA | | | |
|---|---|---|---|---|---|---|---|---|
| Mouse # | Pre-bleed | Bleed1 | Bleed2 | Bleed3 | Pre-bleed | Bleed1 | Bleed2 | Bleed3 |
| 1R | 0002 | 0.009 | 0.057 | 0.770 | 0.003 | 0.003 | 0.006 | 0.175 |
| 2R | 0.008 | 0.003 | 0.474 | 1.285 | 0.009 | 0.012 | 0.005 | 1.354 |
| 1L | 0.002 | 0.006 | 0.036 | 1.025 | 0.048 | 0.014 | 0.005 | 0.384 |
| 2L | 0.03 | 0.002 | 0.135 | 0.697 | 0.024 | 0.006 | 0.041 | 0.127 |
| 0 | 0.005 | 0.010 | 0.106 | 1.99 | 0.004 | 0.009 | 0.009 | 0.700 |

Immunization titers showed a significant increase in 2,4-TDI-HSA specific antibodies for all the mice. Sera polyclonal antibody reactivity towards 2,6-TDI-HSA is much lower when compared to the 2,4-TDI-HSA from 2,4 TDI-KLH immunized mice. Mice immunized with 2,6 TDI-KLH or MDI-KLH are screened as above but using the respective hapten-specific conjugates.

TABLE III

Polyclonal cross reactivity after 3$^{rd}$ immunization

| Mouse # | KLH | KLH-2,4TDI | HSA | HSA-2,4TDI | HSA-2,6TDI | MSA | MSA-2,4TDI | MSA-2,6TDI |
|---|---|---|---|---|---|---|---|---|
| 1R | 3.920 | 4.091 | 0.016 | 0.480 | 0.019 | 0.185 | 0.672 | 0.198 |
| 2R | 4.105 | 4.231 | 0.012 | 2.249 | 0.055 | 0.175 | 3.150 | 0.183 |
| 1L | 3.863 | 3.930 | 0.014 | 0.307 | 0.048 | 0.171 | 0.463 | 0.165 |
| 2L | 3.914 | 4.101 | 0.013 | 0.944 | 0.033 | 0.167 | 1.342 | 0.158 |
| 0 | 4.231 | 4.254 | 0.026 | 0.586 | 0.586 | 0.166 | 0.936 | 0.136 |

Table III shows the cross reactivity screening of the polyclonal mouse sera from 2,4 TDI-KLH sensitized mice. It demonstrates that the polyclonal mouse sera are carrier protein independent since TDI is specifically recognized regardless of the type of carrier protein i.e. HSA, MSA or KLH. There is no significant binding to unconjugated human or mouse serum albumin.

Monoclonal Antibody Production

A final boost of 50 µg is given three days prior to hybridoma production. Cell cultures are maintained in Dulbecco's Modified Eagle Medium. Positive clones are identified using 1 µg/mL 2,4-TDI-HSA as solid phase antigen using the above alkaline-phosphatase-based indirect ELISA. Mouse 1R died before the spleen could be harvested.

On average, 87% of the ELISA wells that are seeded with the fusion product contained growing cell clones with an average of 2.3 clones per well. On average, 0.44% of the seeded wells are positive for anti-TDI-protein-reactive IgG. After fusion, some of the hybridomas are not viable and are lost during the screening process. Thirty-six cell clones are positive against 2,4-TDI-HSA and these are cloned twice by limiting dilution. Resulting stable hybridomas are stored in liquid nitrogen.

TABLE IV

| | Fusion results | | |
|---|---|---|---|
| Mouse | % of wells with growth | Number of clones per well | % of positive clones |
| 1R | 0 | 0 | 0 |
| 2R | 87.3 | 2.2 | 0.118 |
| 1L | 97.4 | 2.41 | 0.3823 |
| 2L | 72.4 | 1.75 | 0 |
| 0 | 92 | 2.71 | 1.25 |

Monoclonal Antibody Quantification and Isotyping

The collected supernatant fluids are stored at 4° C. until characterization. Antibody concentrations in the culture supernatants range from 0.160 µg/mL to 169 µg/mL with an average concentration of 52 µg/mL. 7 mabs react with 2,4 TDI RSA, 1 mAb react 2,6 TDI-HSA only, whilst 46 are found to react with 2,4 and 2,6 TDI HSA conjugates. Of those characterized, 29 hybridomas are found to be IgG1, 14 IgG2a, 4 IgG2b, 2 IgG3 and 3 IgM.

TABLE V

| | | Monoclonal antibody partial characterization | | | | | | | |
|---|---|---|---|---|---|---|---|---|---|
| Mouse | Clone | 2,4 TDI-HSA | 2,6 TDI-HSA | IgG1 | IgG2a | IgGb | IgG3 | IgM | Concentration µg/ml |
| 2,4 TDI- KLH Mice | 2E5 | ✓ | | | ✓ | | | | 39 |
| | 10C2 | ✓ | | | ✓ | | | | 101 |
| | 40C6 | ✓ | ✓ | | | ✓ | | | 21 |
| | 41B9 | ✓ | | | ✓ | | | | 95 |
| | 42E2 | ✓ | ✓ | ✓ | | | | | 52 |
| | 43B4 | ✓ | ✓ | ✓ | | | | | 169 |
| | 43G6 | ✓ | ✓ | ✓ | | | | | 65 |
| | 46G10 | ✓ | ✓ | | | | ✓ | | 27 |
| | 49B10 | ✓ | ✓ | ✓ | | | | | 70 |
| | 50B5 | ✓ | ✓ | ✓ | | | | | 23 |
| | 50F8 | ✓ | ✓ | ✓ | | | | | 100 |
| | 51E6 | ✓ | ✓ | ✓ | | | | | 48 |
| | 52G11 | ✓ | ✓ | ✓ | | | | | 40 |
| | 56G8 | ✓ | | | ✓ | | | | 16 |
| | 57B5 | ✓ | ✓ | ✓ | | | | | 59 |
| | 57D5 | ✓ | ✓ | | ✓ | | | | 11 |
| | 57F2 | ✓ | | | ✓ | | | | 37 |
| | 58E9 | ✓ | ✓ | ✓ | | | | | 91 |
| | 59B3 | ✓ | | | ✓ | | | | 31 |
| | 60D10 | ✓ | ✓ | | ✓ | | | | 23 |
| | 60G2 | ✓ | ✓ | ✓ | | | | | 104 |
| | 61C2 | ✓ | ✓ | | ✓ | | | | 33 |
| | 62E4 | ✓ | ✓ | ✓ | | | | | 52 |
| | 62G5 | ✓ | ✓ | | ✓ | | | | 17 |
| | 63D3 | ✓ | ✓ | ✓ | | | | | 29 |
| | 66C2 | ✓ | ✓ | ✓ | | | | | 51 |
| | 66F7 | ✓ | ✓ | ✓ | | | | | 60 |
| | 66F10 | ✓ | ✓ | ✓ | | | | | 32 |
| | 67C4 | ✓ | | | ✓ | | | | 32 |
| | 73F11 | ✓ | ✓ | | ✓ | | | | 46 |
| | 75C8 | ✓ | ✓ | ✓ | | | | | 75 |
| | 75E4 | ✓ | ✓ | ✓ | | | | | 74 |
| | 77E6 | ✓ | ✓ | ✓ | | | | | 80 |
| | 79C7 | ✓ | | | ✓ | | | | 35 |
| | 79G3 | ✓ | ✓ | | | | ✓ | | 39 |
| | 79G7 | ✓ | ✓ | | ✓ | | | | 33 |
| 2,6 TDI- KLH Mice | 16C6 | ✓ | ✓ | ✓ | | | | | 56 |
| | 31F2 | ✓ | ✓ | | ✓ | | | | 20 |
| | 32B6 | ✓ | ✓ | ✓✓ | | | | | 71 |
| | 53C2 | ✓ | ✓ | | ✓ | | | | 34 |
| | 53C6 | ✓ | ✓ | ✓ | | | | | 88 |
| | 54F8 | ✓ | ✓ | | | ✓ | | | 85 |
| | 57G8 | ✓ | ✓ | | | ✓ | | | 66 |
| | 59E5 | | ✓ | | | | ✓ | | 6 |
| | 60C5 | ✓ | ✓ | ✓ | | | | | 10 |
| | 60C11 | ✓ | ✓ | ✓ | | | | | 70 |
| | 68D3 | ✓ | ✓ | | | | ✓ | | 38 |
| | 68E4 | ✓ | ✓ | | ✓ | | | | 134 |
| | 68D5 | ✓ | ✓ | | ✓ | | | | 130 |

TABLE V-continued

Monoclonal antibody partial characterization

| Mouse | Clone | 2,4 TDI-HSA | 2,6 TDI-HSA | IgG1 | IgG2a | IgGb | IgG3 | IgM | Concentration µg/ml |
|---|---|---|---|---|---|---|---|---|---|
| TDI Vapor Exposed Mice | 16F4 | ✓ | ✓ | | | | | ✓ | 0.164 |
| | 29E5 | ✓ | ✓ | | | | | ✓ | 0.160 |
| | 56F6 | ✓ | ✓ | | | | | ✓ | 0.467 |
| MDI-KLH Mice | 55D5 | ✓ | ✓ | | | | | | |
| | 64D2 | ✓ | ✓ | | | | | | |

Immunoblot Characterization of Monoclonal Antibodies

Selected antibodies are also characterized using immunoblot techniques and the results are shown in FIGS. 4A and 4B. Antibodies from clone 2E5 are specific for 2,4-TDI-HSA. IgG from clone 60G2 reacts with both 2,4- and 2,6-TDI-HSA and has also little cross reactivity with HDI/MDI conjugated HSA. This may be due to the antigen binding site of the mAb also recognizing the urea bond between the protein and dNCO. In this Western blot the proteins are denatured confirming that the monoclonals are protein-conformation independent. The blots also show extensive polymerization and dimerization of the conjugates as shown by binding at molecular weight equivalences of around 150 kDa and above. Antibody staining indicating molecular weights less than that of HSA (66679 Da) are most likely attributable to intramolecular TDI cross-linking of the HSA molecule. Such cross-linking may prevent complete protein denaturation and result in higher electrophoretic mobility and thus faster migration of the molecule through the gel.

Example

TDI Vapor Exposure of Mice for Antibody Production

Female specific-pathogen-free inbred C57BL/6 mice are purchased from Jackson Laboratories (Bar Harbor, Me.) at 5 to 6 weeks of age. Upon arrival the mice are quarantined for 2 weeks and acclimated to a 12-hour light/dark cycle. Animals are housed in ventilated microisolator cages in environmentally controlled conditions at NIOSH animal facilities in compliance with AAALAC approved guidelines and an approved IACUC protocol. The animal rooms are monitored for specific pathogens through disease surveillance and a sentinel animal program. Food and water are provided ad libitum.

TDI Exposure System

Toluene diisocyanate (TDI; Mondur TD80 Grade A; 80% and 20% mixture of 2,4- and 2,6-isomers, respectively) is provided by Bayer Corporation, Polyurethanes Division (Pittsburgh, Pa.). The TDI exposure system has been described in detail previously in Johnson et al., 2007, The Journal of Immunology, 179:1864-1871. Briefly, mice are exposed in a 1200 L stainless steel live-in chamber (Unifab Corporation, Kalamazoo, Mich.) supplied with HEPA purified and conditioned air providing nine air changes per hour and maintaining temperature and humidity at 23±2° C. and 50±5%, respectively. Mice are housed in hanging stainless steel mesh cages and remained in the chambers continuously from Monday morning through Friday afternoon and are returned to microisolator cages over the weekend. Generation of a TDI vapor atmosphere that was free of TDI aerosol is achieved by passing dried HEPA filtered air over a 50 $cm^2$ surface of liquid TDI which is mixed and diluted with the dilution air flow. The TDI concentration (50±5 ppb) in the chamber is continuously monitored using RIS T (Remote Intelligent Sensor) DI analyzers (Scott Safety and Health, Monroe, N.C.). The RIS units were calibrated using a fluorescamine assay with a detection limit of 10 ng/ml as described in Johnson et al., 2007, The Journal of Immunology, 179:1864-1871. Mice are exposed to TDI vapor for 4 h/day, for 12 consecutive work days. Lymph nodes and spleen tissue are collected 24 hrs following the final exposure.

Anti-TDI IgM mAbs producing clones are produced from the exposed animals. These mAbs have been characterized by the same methods used to characterize the IgG mAbs and show good reactivity toward TDI-, MDI- and HDI-protein conjugates.

Example

Physiological Relevance of Produced Mabs

Figure 5:
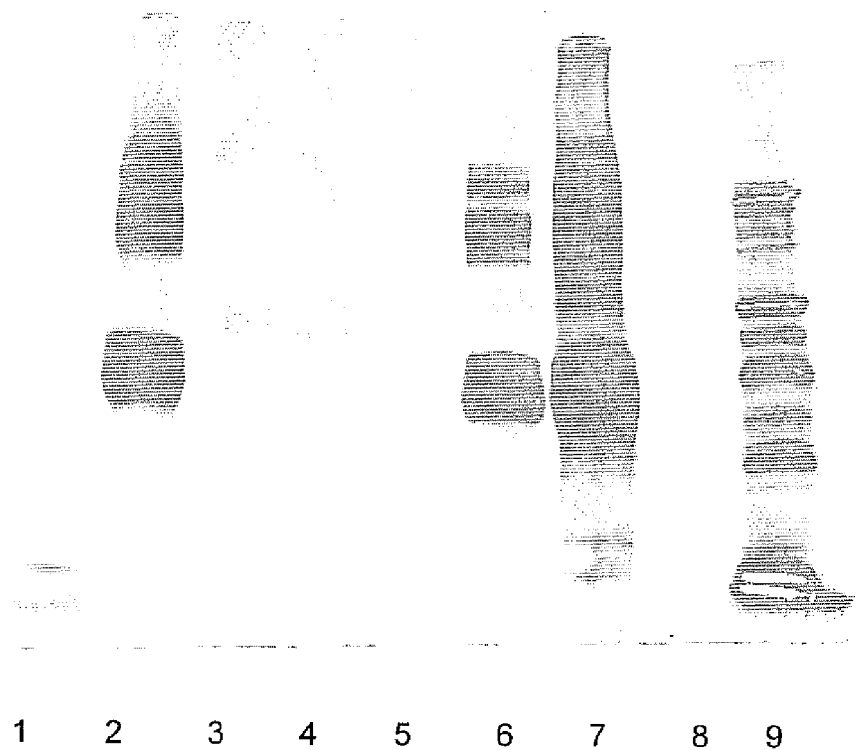
FIG. 5 shows a Western blot demonstrating binding specificity of mAbs of the present invention with diisocyanate-protein conjugates from TDI vapor exposed cells and protein.

FIG. 5 shows a Western blot and demonstrates binding specificity of mAbs of the present invention with diisocyanate-protein conjugates.

For this example, mouse albumin solution or extracts of A549 immortal human lung epithelial cells are exposed to 50 ppb TDI by passive diffusion (lanes 2, 3, 4 and 7) for 1 hr unless otherwise indicated; or at a flow of 200 mL/min (lane 6) for 1 hr using the Vitrocell exposure system (Vitrocell Systems GmbH, Waldkirch, Germany). Following exposure protein is extracted from the cells for analyses.

Western Blot of the TDI Vapor Exposed Mouse Albumin (MSA) and Human Lung Epithelial Cells A549 is performed with anti-TDI-protein mAb 60G2 and results are shown in FIG. 5. The image in FIG. 5 shows Lanes: 1) Pre-stained MW Markers, 2) MSA-TDI passive diffusion, 3 and 4) A549 Cells—TDI passive diffusion, 5) MSA TDI 20 mL/min, 6) MSA TDI 200 mL/min, 7) MSA, TDI passive diffusion—4 hrs, 8) Unexposed MSA negative control, 9) Pre-stained MW Marker Set 2. Dark bands on MSA and cell extract lanes indicate binding of mAb.

FIG. 5 is a representative Western Blot demonstrating mAb binding to cellular TDI bound proteins under physiological conditions. Six mAb have been assessed and found to identify multiple TDI bound lung proteins. These are mAbs 60G2, 62G5, 77E6, 79G7, 67C4 and 66F7.

Reaction of the mAb to TDI vapor exposed MSA is exposure-dose dependent. Vapor exposure of the lung cells mimics that expected of inhalation vapor exposure of man demonstrating the utility of the mAb to react to cellular proteins bound by TDI vapor.

Example

ELISA Analysis

FIG. 6 shows results of ELISA analysis of 9 monoclonal antibodies against diisocyanate-conjugated proteins. mAbs are grouped into one of eight different groups based on their reactivity patterns. Representative reactivities in ELISA are provided. All chemicals noted are reacted to the protein listed in column 3 to provide the specific hapten for testing. The results represent the mean OD450 of 2 ELISA replicate wells corrected for background binding. mAbs 2E5, 60G2, 62G5 and 59G5 groups are from 2,4 TDI-KLH immunized mice, whilst 32B6 and 59E6 groups are from 2,6 TDI-KLH immunized mice. The 16F4 group are IgM mAbs from TDI vapor exposed mice and the 64D2 group are IgG mAbs from MDI-KLH immunized mice.

The results represent the mean OD450 of 4 ELISA well repeats which are corrected by subtracting the average OD of 4 ELISA background control wells. Assay background controls are processed in parallel but contained HSA as the coating antigen. Positive values are considered to be 3 times the OD450 value of HSA and their value reported. 2E5, 62G5, 60G2 and 79G7 are from 2,4 TDI-KLH immunized mice, whilst 16C6, 32B6 and 59E6 are from 2,6TDI-KLH immunized mice and 16F4 and 29E5 are from TDI vapor exposed mice.

Example

Western Blot Analysis of mAbs Reactivity

FIGS. 4A and 4B shows results of Western blot analysis of mAbs reactivity. In this example, protein-isocyanate conjugates are separated by SDS-PAGE (5 μg/lane, 7.5% separation gels) and transferred overnight at 15 mA to nitrocellulose membranes (0.2 μm, Biorad, Hercules, Calif.). The membranes are blocked with 3% BSA in PBST for 1 hr before being reacted with a 1/10 dilution of mAb CSNs for 1 hr. After washing, the blot is incubated with Biotin-SP-conjugated Affinity Pure goat anti-mouse IgM secondary antibody (Jackson Immuno Research Laboratories, Inc., West Grove, Pa.) for 1 h at 37° C. at a dilution of 1/5000 in PBSTM. Immune complexes were labeled with alkaline phosphatase-conjugated streptavidin (Jackson Immuno Research Laboratories, Inc., West Grove, Pa.) by incubating a 1/5000 dilution in PBSTM for 1 h at 37° C. Protein bands were visualized using a nitroblue tetrazolium/bromo-chloro-indolyl phosphate substrate reagent kit (NBT/BLIP Promega, Madison, Wis.). Color was allowed to develop for 5 min and stopped by washing the membranes with distilled/deionized $H_2O$.

Dot Blot Analysis

A dot blot analysis is carried out to analyse reactivity of mAbs. Briefly TDI-Conjugates (4 μl of 5 μg/mL of native or denatured antigen per spot) are spotted to Nitrocellulose membrane (0.2 μm, BioRad) and allowed to dry overnight. All the other steps are identical to western blot protocol for incubations and color development.

Figure 8A:
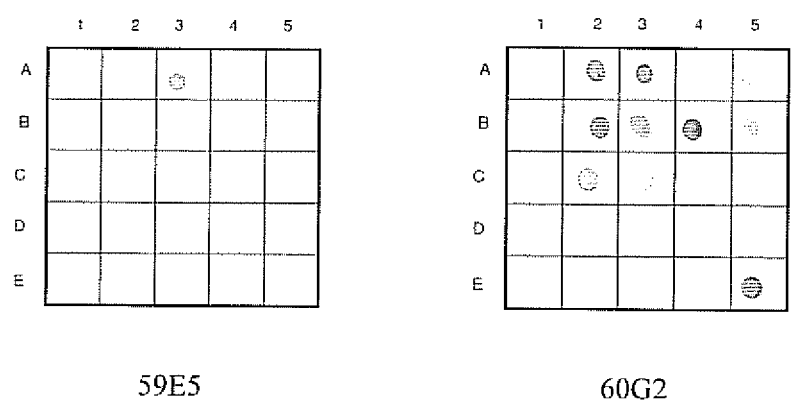

FIGS. 5A and 8B show results of a dot blot analysis. Key for Antigen Location on the Dot Blot:

| | | |
|---|---|---|
| Lane A1: HSA | Lane A2: HSA-2,4 TDI | Lane A3: HSA-2,6 TDI |
| Lane A4: HSA-HDI | Lane A5: HSA-MDI | Lane B1: KLH |
| Lane B2: KLH-2,4 TDI | Lane B3: KLH-2,6 TDI | Lane B4: MSA-2,4 TDI |
| Lane B5: MSA-2,6 TDI | Lane C1: MSA | Lane C2: Keratin-2,4 TDI |
| Lane C3: Keratin-2,6 TDI | Lane C4: Keratin | Lane C5: Lysozyme-2,4 TDI |
| Lane D1: Lysozyme | Lane D2: lysozyme-2,6 TDI | Lane D3: HSA-OTI |
| Lane D4: HSA-2,5 DMPI | Lane D5: HSA-3,4 DMPI | Lane E1: Collagen |
| Lane E2: Collagen-2,4 TDI | Lane E3: Collagen 2,6 TDI | Lane E4: HSA-Gorrilla glue |
| Lane E5: HSA-2,4; 2,6 TDI (industrial) | | |

REFERENCES

1. Karol, M. H. Respiratory Effects of Inhaled Isocyanates. *Crc Critical Reviews in Toxicology* 1986, 16, 349-379.
2. Wisnewski, A. V.; Srivastava, R.; Herick, C.; Xu, L.; Lemus, R.; Cain, H.; Magoski, N. M.; Karol, M. H.; Bottomly, K.; Redlich, C. A. Identification of human lung and skin proteins conjugated with hexamethylene diisocyanate in vitro and in vivo. *Am. J. Respir. Crit. Care Med.* 2000, 162, 2330-2336.
3. Johannesson, G.; Sennbro, C. J.; Willix, P.; Lindh, C. H; Jonsson, B. A. Identification and characterisation of adducts between serum albumin and 4,4'-methylenediphenyl diisocyanate (MDI) in human plasma. *Arch. Toxicol.* 2004, 78, 378-383.
4. Kristiansson, M. H.; Lindh, C. H.; Jonsson, B. A. G. Determination of hexahydrophthalic anhydride adducts to human serum albumin. *Biomarkers* 2003, 8, 343-359.
5. Mraz, J.; Bouskova, S. 2,4-toluenediisocyanate and hexamethylene-diisocyanate adducts with blood proteins: assessment of reactivity of amino acid residues in vitro. *Chem. Biol. Interact.* 1999, 117, 173-186.
6. Redlich, C. A.; Karol, M. H.; Graham, C.; Horner, R. J.; Holm, C. T.; Wirth, J. A.; Cullen, M. R. Airway isocyanate-adducts in asthma induced by exposure to hexamethylene diisocyanate. *Scand. J. Work Environ. Health* 1997, 23, 227-231.
7. Wisnewski, A. V.; Liu, Q.; Liu, J.; Redlich, C. A. Human innate immune responses to hexamethylene diisocyanate (HDI) and HDI-albumin conjugates. *Clin. Exp. Allergy* 2008, 38, 957-967.
8. Wisnewski, A. V.; Stowe, M. H.; Cartier, A.; Liu, Q.; Liu, J.; Chen, L.; Redlich, C. A. Isocyanate vapor-induced antigenicity of human albumin. *J. Allergy Clin. Immunol.* 2004, 113, 1178-1184.
9. Wisnewski, A. V.; Lemus, R.; Karol, M. H.; Redlich, C. A. Isocyanate-conjugated human lung epithelial cell proteins: A link between exposure and asthma? *J. Allergy Clin. Immunol.* 1999, 104, 341-347.
10. Wisnewski, A. V.; Liu, Q.; Liu, J.; Redlich, C. A. Glutathione protects human airway proteins and epithelial cells from isocyanates. *Clin. Exp. Allergy* 2005, 35, 352-357.
11. Ye, Y. M.; Nahm, D. H.; Kim, C. W.; Kim, H. R.; Hong, C. S.; Park, C. S.; Suh, C. H.; Park, H. S. Cytokeratin autoantibodies: useful serologic markers for toluene diisocyanate-induced asthma. *Yonsei Med. J.* 2006, 47, 773-781.

12. Guide for the Care and Use of Laboratory Animals; National Academy Press: Washington, D.C, 1996.
13. Ulrich, H. *Chemistry and Technology of Isocyanates*; John Wiley and Sons: New York, 1996; pp 315-456.
14. Kirk-Othmer Isocyanates, Organic. In *Kirk-Othmer encyclopedia of chemical technology*, 4 ed.; Chadwick, D. H.; Cleveland, T. H. Eds.; Wiley-Interscience: Hoboken, 2001; pp 902-931.
15. Brown, W. E.; Green, A. H.; Cedel, T. E.; Cairns, J. Biochemistry of Protein-Isocyanate Interactions—A Comparison of the Effects of Aryl Vs Alkyl Isocyanates. *Environmental Health Perspectives* 1987, 72, 5-11.
16. Allport, D. C.; Gilbert, D. S.; Outterside, S. M. *MDI and TDI:Safety, Health and the Environment: A Source Book and Practical Guide;* Wiley: 2003.
17. Holgate, S. T. Pathogenesis of asthma. Clin. Exp. Allergy 2008, 38, 872-897.
18. Lemanske, R. F., Jr.; Busse, W. W. 6. Asthma. *J. Allergy Clin. Immunol.* 2003, 111, S502-S519.
19. Lange, R. W.; Lantz, R. C.; Stolz, D. B.; Watkins, S. C.; Sundareshan, P.; Lemus, R.; Karol, M. H. Toluene diisocyanate colocalizes with tubulin on cilia of differentiated human airway epithelial cells. *Toxicol. Sci.* 1999, 50, 64-71.
20. Ott, M. G.; Jolly, A. T.; Burkert, A. L.; Brown, W. E. Issues in diisocyanate antibody testing. *Critical Reviews in Toxicology* 2007, 37, 567-585.
21. Wisnewski, A. V.; Redlich, C. A. Recent developments in diisocyanate asthma. *Curr. Opin. Allergy Clin. Immunol.* 2001, 1, 169-175.
22. Herrick, C. A.; Xu, L.; Wisnewski, A. V.; Das, J.; Redlich, C. A.; Bottomly, K. A novel mouse model of diisocyanate-induced asthma showing allergic-type inflammation in the lung after inhaled antigen challenge. *J. Allergy Clin. Immunol.* 2002, 109, 873-878.
23. Chipinda, I.; Stetson, S. J.; Depree, G. J.; Simoyi, R. H.; Siegel, P. D. Kinetics and mechanistic studies of the hydrolysis of diisocyanate-derived bis-thiocarbamates of cysteine methyl ester. *Chemical Research in Toxicology* 2006, 19, 341-350.
24. Park, H. S.; Lee, S. K.; Kim, H. Y.; Nahm, D. H.; Kim, S. S. Specific immunoglobulin E and immunoglobulin G antibodies to toluene diisocyanate-human serum albumin conjugate: useful markers for predicting long-term prognosis in toluene diisocyanate-induced asthma. *Clin. Exp. Allergy* 2002, 32, 551-555.
25. Karol, M. H.; Ioset, H. H.; Alarie, Y. C. Tolyl-specific IgE antibodies in workers with hypersensitivity to toluene diisocyanate. *Am. Ind. Hyg. Assoc. J.* 1978, 39, 454-458.
26. Cartier, A.; Grammer, L.; Malo, J. L.; Lagier, F.; Ghezzo, H.; Harris, K.; Patterson, R. Specific serum antibodies against isocyanates: association with occupational asthma. *J. Allergy Clin. Immunol.* 1989, 84, 507-514.
27. Campo, P.; Wisnewski, A. V.; Lummus, Z.; Cartier, A.; Malo, J. L.; Boulet, L. P.; Bernstein, D. I. Diisocyanate conjugate and immunoassay characteristics influence detection of specific antibodies in HDI-exposed workers. *Clin. Exp. Allergy* 2007, 37, 1095-1102.
28. Son, M.; Lee, M.; Kim, Y. T.; Youn, J. K.; Park, H. Heterogeneity of IgE response to TDI-HSA conjugates by ELISA in toluene diisocyanate (TDI)-induced occupational asthma (OA) patients. *J. Korean Med. Sci.* 1998, 13, 147-152.
29. Tee, R. D.; Cullinan, P.; Welch, J.; Burge, P. S.; Newman-Taylor, A. J. Specific IgE to isocyanates: a useful diagnostic role in occupational asthma. *J. Allergy Clin. Immunol.* 1998, 101, 709-715.
30. Welinder, H.; Nielsen, J.; Bensryd, I.; Skerfving, S. IgG antibodies against polyisocyanates in car painters. *Clin. Allergy* 1988, 18, 85-93.
31. Jones, M. G.; Floyd, A.; Nouri-Aria, K. T.; Jacobson, M. R.; Durham, S. R.; Taylor, A. N.; Cullinan, P. Is occupational asthma to diisocyanates a non-IgE-mediated disease? *J. Allergy Clin. Immunol.* 2006, 117, 663-669.
32. Park, H. S.; Kim, H. Y.; Nahm, D. H.; Son, J. W.; Kim, Y. Y. Specific IgG, but not specific IgE, antibodies to toluene diisocyanate-human serum albumin conjugate are associated with toluene diisocyanate bronchoprovocation test results. *J. Allergy Clin. Immunol.* 1999, 104, 847-851.
33. Bernstein, D. I.; Ott, M. G.; Woolhiser, M.; Lummus, Z.; Graham, C. Evaluation of antibody binding to diisocyanate protein conjugates in a general population. *Ann. Allergy Asthma Immunol.* 2006, 97, 357-364.
34. Pauluhn, J.; Brown, W. E.; Hext, P.; Leibold, E.; Leng, G. Analysis of biomarkers in rats and dogs exposed to polymeric methylenediphenyl diisocyanate (pMDI) and its glutathione adduct. *Toxicology* 2006, 222, 202-212.
35. Brown, W. E.; Burkert, A. L. Biomarkers of toluene diisocyanate exposure. *Appl. Occup. Environ. Hyg.* 2002, 17, 840-845.
36. Wisnewski, A. V. Developments in laboratory diagnostics for isocyanate asthma. *Curr. Opin. Allergy Clin. Immunol.* 2007, 7, 138-145.
37. Lemus, R.; Lukinskeine, L.; Bier, M. E.; Wisnewski, A. V.; Redlich, C. A.; Karol, M. H. Development of immunoassays for biomonitoring of hexamethylene diisocyanate exposure. *Environ. Health Perspect.* 2001, 109, 1103-1108.
38. Nethercott J. R. Practical Problems in the Use of Patch Testing in Evaluation of Patients with Contact Dermatitis. Current Problems in Dermatology II, 95-123. 1990.
39. Adams R. M Patch Testing Its Technique and Allergen Replacement. In *Occupational Skin Diseases,* 3 edition ed.; W.B Saunders, Philadelphia: 99 A.D.
40. Anne H. Chappelle; Ronald N. Shiotsuka; and Micheal J. Bartels. Some Limitations in the Use of Urine Biomonitering for Measuring TDI Exposure. Isocyanates:Sampling, Analysis and Health Effects. 64-74. 2008. West Conshohocken, Pa. ASTM STP 1408.
41. Sennbro, C. J.; Lindh, C. H.; Tinnerberg, H.; Welinder, H.; Littorin, M.; Jonsson, B. A. Biological monitoring of exposure to toluene diisocyanate. *Scand. J. Work Environ. Health* 2004, 30, 371-378.
42. Tinnerberg, H.; Dalene, M.; Skarping, G. Air and biological monitoring of toluene diisocyanate in a flexible foam plant. *Am. Ind. Hyg. Assoc. J.* 1997, 58, 229-235.
43. Dalene, M.; Skarping, G.; Tinnerberg, H. Biological monitoring of hexamethylene diisocyanate by determination of 1,6-hexamethylene diamine as the trifluoroethyl chloroformate derivative using capillary gas chromatography with thermoionic and selective-ion monitoring. *J. Chromatogr. Biomed Appl.* 1994, 656, 319-328.
44. Sabbioni, G.; Beyerbach, A. Haemoglobin adducts of aromatic amines: diamines and polyaromatic amines. *Journal of Chromatography B-Analytical Technologies in the Biomedical and Life Sciences* 2000, 744, 377-387.
45. Tinnerberg, H.; Mattsson, C. Usage of air monitoring and biomarkers of isocyanate exposure to assess the effect of a control intervention. *Ann. Occup. Hyg* 2008, 52, 187-194.
46. Sabbioni, G.; Hartley, R.; Henschler, D.; Hollrigl-Rosta, A.; Koeber, R.; Schneider, S. Isocyanate-specific hemoglobin adduct in rats exposed to 4,4'-methylenediphenyl diisocyanate. *Chemical Research in Toxicology* 2000, 13, 82-89.

47. Habeeb, A. F.; Cassidy, H. G.; Singer, S. J. Molecular structural effects produced in proteins by reaction with succinic anhydride. *Biochim. Biophys. Acta* 1958, 29, 587-593.
48. Stoscheck, C. M. Quantitation of protein. *Methods Enzymol.* 1990, 182, 50-68.
49. Lowry, O. H.; Rosebrough, N. J.; Farr, A. L.; Randall, R. J. Protein measurement with the Folin phenol reagent. *J. Biol. Chem.* 1951, 193, 265-275.
50. Bradford, M. M. A rapid and sensitive method for the quantitation of microgram quantities of protein utilizing the principle of protein-dye binding. *Anal. Biochem.* 1976, 72, 248-254.
51. Zor, T.; Selinger, Z. Linearization of the Bradford protein assay increases its sensitivity: theoretical and experimental studies. *Anal. Biochem.* 1996, 236, 302-308.
52. Sashidhar, R. B.; Capoor, A. K.; Ramana, D. Quantitation of Epsilon-Amino Group Using Amino-Acids As Reference-Standards by Trinitrobenzene Sulfonic-Acid—A Simple Spectrophotometric Method for the Estimation of Hapten to Carrier Protein Ratio. *Journal of Immunological Methods* 1994, 167, 121-127.
53. Bernstein, D. I.; Zeiss, C. R. Guidelines for preparation and characterization of chemical-protein conjugate antigens. Report of the Subcommittee on Preparation and Characterization of Low Molecular Weight Antigens. *J. Allergy Clin. Immunol.* 1989, 84, 820-822.
54. Steven L. Snyder; Philip Z. Sobocinski. An improved 2,4,6-trinitrobenzenesulphonic acid method for the determination of amines. Analytical Biochemistry 64[1], 284-288. 1975.
55. Lateef, S. S.; Gupta, S.; Jayathilaka, L. P.; Krishnanchettiar, S.; Huang, J. S.; Lee, B. S. An improved protocol for coupling synthetic peptides to carrier proteins for antibody production using DMF to solubilize peptides. *J. Biomol. Tech.* 2007, 18, 173-176.
56. Hornbeck, P.; Winston, S. E.; Fuller, S. A. Enzyme-linked immunosorbent assays (ELISA). *Curr. Protoc. Mal. Biol.* 2001, Chapter 11, Unit 11.
57. Hornbeck, P. Enzyme-linked immunosorbent assays. *Curr. Protoc. Immunol.* 2001, Chapter 2, Unit.
58. Goldsby, R. A.; Kindt, T. J.; Osborne, B. A. *Kuby Immunology*; W.H Freeman and Company: New York, 2000; p 108.
59. Monoclonal Antibody Production: A Report of the Committee on Methods of Producing Monoclonal Antibodies, Institute for Laboratory Animal Research, National Research Council. 1-57. 1999. Washington, D.C., National Academy of Sciences.
60. Fuller, S. A.; Takahashi, M.; Hurrell, J. G. Fusion of myeloma cells with immune spleen cells. *Curr. Protoc. Mol. Biol.* 2001, Chapter 11, Unit 11.
61. Fuller, S. A.; Takahashi, M.; Hurrell, J. G. Cloning of hybridoma cell lines by limiting dilution. *Curr. Protoc. Mol. Biol.* 2001, Chapter 11, Unit 11.
62. Fuller, S. A.; Takahashi, M.; Hurrell, J. G. Cloning of hybridoma cell lines by limiting dilution. *Curr. Protoc. Mal. Biol.* 2001, Chapter 11, Unit 11.
63. Fuller, S. A.; Takahashi, M.; Hurrell, J. G. Freezing and recovery of hybridoma cell lines. *Curr. Protoc. Mol. Biol.* 2001, Chapter 11, Unit 11.
64. Cooper, H. M.; Paterson, Y. Determination of the specific antibody titer. *Curr. Protoc. Mol. Biol.* 2001, Chapter 11, Unit 11.
65. Takahashi, S.; Yamamura, T.; Kamo, M.; Satake, K. Regeneration of Amino-Compounds from the 2,4,6-Trinitrophenyl Derivatives by Treatment with Hydrazine. *Chemistry Letters* 1984, 127-130.
66. Harlow, E. a. L. D. Antibodies—A laboratory Manual.; Cold Spring Harbor Laboratory Press: Cold Spring Harbor, N.Y., 1988.
67. Schmechel, D.; Simpson, J. P.; Beezhold, D.; Lewis, D. M. The development of species-specific immunodiagnostics for *Stachybotrys chartarum*: The role of cross-reactivity. *Journal of Immunological Methods* 2006, 309, 150-159.

Any patents or publications mentioned in this specification are incorporated herein by reference to the same extent as if each individual publication is specifically and individually indicated to be incorporated by reference.

The compositions, methods and kits described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A method of detecting diisocyanate-protein conjugates in a sample, comprising:
   a) contacting a sample with a first isolated monoclonal antibody or antigen binding fragment thereof, wherein the first isolated monoclonal antibody or antigen binding fragment thereof binds to a 2,4-toluene diisocyanate moiety bound to a protein through a urea, urethane, carbamate or thiocarbamate linkage; and
   b) detecting binding of the first isolated monoclonal antibody or antigen binding fragment thereof with the 2,4-toluene diisocyanate moiety bound to a protein through a urea, urethane, carbamate or thiocarbamate linkage, and
   c) contacting the sample with a second monoclonal antibody or antigen binding fragment thereof wherein the second monoclonal antibody or antigen binding fragment thereof binds to 2,6-toluene diisocyanate moiety bound to a protein through a urea, urethane, carbamate or thiocarbamate linkage; and
   d) detecting binding of the second isolated monoclonal antibody or antigen binding fragment thereof with the 2,6-toluene diisocyanate moiety bound to a protein through a urea, urethane, carbamate or thiocarbamate linkage.

2. The method of claim 1, further comprising: contacting the sample with a third monoclonal antibody or antigen binding fragment thereof wherein the third monoclonal antibody or antigen binding fragment thereof binds to a diisocyanate moiety bound to a protein through a urea, urethane, carbamate or thiocarbamate linkage; and
   detecting the binding of the third monoclonal antibody or antigen binding fragment thereof with the diiscyanate moiety bound to a protein through a urea, urethane, carbamate or thiocarbamate linkage.

3. The method of claim 1, wherein the sample is obtained from a mammalian subject.

4. The method of claim 3, wherein the subject is human.

5. The method of claim 1, wherein the sample is an environmental sample.

* * * * *